(12) United States Patent
Akahori et al.

(10) Patent No.: US 10,294,525 B2
(45) Date of Patent: May 21, 2019

(54) BIOMOLECULE MEASUREMENT SYSTEM AND BIOMOLECULE MEASUREMENT METHOD

(71) Applicant: HITACHI HIGH-TECHNOLOGIES CORPORATION, Tokyo (JP)

(72) Inventors: Rena Akahori, Tokyo (JP); Itaru Yanagi, Tokyo (JP); Kenichi Takeda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/531,500

(22) PCT Filed: Oct. 28, 2015

(86) PCT No.: PCT/JP2015/080402
§ 371 (c)(1),
(2) Date: May 30, 2017

(87) PCT Pub. No.: WO2016/088486
PCT Pub. Date: Jun. 9, 2016

(65) Prior Publication Data
US 2017/0268054 A1 Sep. 21, 2017

(30) Foreign Application Priority Data
Dec. 4, 2014 (JP) ................................. 2014-246163

(51) Int. Cl.
*C12Q 1/6869* (2018.01)
*G01N 27/447* (2006.01)
*G01N 33/487* (2006.01)

(52) U.S. Cl.
CPC ..... *C12Q 1/6869* (2013.01); *G01N 27/44791* (2013.01); *G01N 33/48721* (2013.01)

(58) Field of Classification Search
CPC ........... C12Q 1/6869; G01N 33/48721; G01N 27/44791
See application file for complete search history.

(56) References Cited

U.S. PATENT DOCUMENTS

2005/0112317 A1  5/2005  McCarthy et al.
2005/0112617 A1* 5/2005  Diessel ................ C12Q 1/6816
                                                            435/6.11
(Continued)

FOREIGN PATENT DOCUMENTS

JP  2006-078491 A   3/2003
JP  2011-211905 A  10/2011
KR  20130056756 A   5/2013

OTHER PUBLICATIONS

Chanbae Hyun, et al., "Threading Immobilized DNA Molecules through a Solid-State Nanopore at >100 μs per Base Rate", American Chemical Society, Jun. 11, 2013, vol. 7, No. 7, pp. 5892-5900.
(Continued)

*Primary Examiner* — Melanie Brown
(74) *Attorney, Agent, or Firm* — Mattingly & Malur, PC

(57) ABSTRACT

To introduce a biomolecule into a nanopore without the need to check the position of the nanopore in a thin film. In addition, displacement stability is ensured and stable acquisition of blocking signals is realized. An immobilization member 107 having a larger size than a thin film 113 with a nanopore 112 is used, and biomolecules are immobilized on the biomolecule immobilization member 107 at a density that allows at least one biomolecule 108 to enter an electric field region around the nanopore when the biomolecule immobilization member 107 has moved close to a nanopore device 101.

16 Claims, 22 Drawing Sheets

(56) References Cited

U.S. PATENT DOCUMENTS

| | | | |
|---|---|---|---|
| 2006/0057585 A1 | 3/2006 | McAllister | |
| 2006/0154399 A1* | 7/2006 | Sauer | C12Q 1/6874 |
| | | | 438/48 |
| 2012/0312083 A1 | 12/2012 | Akahori et al. | |
| 2013/0186757 A1* | 7/2013 | Reinhart | C12Q 1/6869 |
| | | | 204/452 |
| 2014/0285224 A1* | 9/2014 | Albuschies | B82Y 40/00 |
| | | | 324/691 |

OTHER PUBLICATIONS

Edward M. Nelson, et al., "Direct, Concurrent Measurements of the Forces and Currents Affecting DNA in a Nanopore with Comparable Topography", American Chemical Society, May 19, 2014, vol. 8, No. 6, pp. 5484-5493.

International Search Report of PCT/JP2015/080402 dated Jan. 26, 2016.

Chinese Office Action received in corresponding Chinese Application No. 201580064266.5 dated Dec. 6, 2018.

* cited by examiner (a)

(b)

(c)

(a)

(b)

(a)

(b)

(a)

(b)

(a)

(b)

(c)

Distance (h) between Nanopore Device and
Biomolecule Immobilization Member (a)

(b)

(c)

(d)

(a)

(b)

(a)

(b)

(a)

(b)

(c)

(a)

(b)

BIOMOLECULE MEASUREMENT SYSTEM AND BIOMOLECULE MEASUREMENT METHOD

TECHNICAL FIELD

The present invention relates to a biomolecule measurement system using a nanopore provided in a thin film, and a biomolecule measurement method.

BACKGROUND ART

As a next-generation DNA sequencer, a method of electrically measuring the base sequence of DNA directly without performing extension reactions or fluorescence labeling has been drawing attention. To that end, a nanopore DNA sequencing method that determines a base sequence by directly measuring a DNA fragment without using a reagent has been actively researched and developed. This method is based on the principle of sequentially identifying the types of individual bases contained in a DNA strand by directly measuring the difference between the types of the bases on the basis of the amounts of blocking currents that flow when the DNA strand passes through a nanopore. Such a method is expected to increase the throughput, reduce the running cost, and be able to determine long sequences of bases since amplification using enzymes of template DNA is not performed, nor is a labeling substance such as a phosphor used.

As a problem of the nanopore method, translocation control for DNA that passes through a nanopore is given. In order to measure the difference between the types of individual bases contained in a DNA strand on the basis of the amounts of blocking currents, it is considered that the speed of the DNA passing through a nanopore should be set to greater than or equal to 100 µs per 1 base in view of current noise generated during measurement and a time constant of fluctuation of DNA molecules. When DNA is sequenced using a nanopore, a potential gradient is formed using electrodes located above and below the nanopore so that negatively charged DNA is allowed to pass through the nanopore. However, the speed of DNA passing through a nanopore is typically as high as less than or equal to 1 µs per base, and it is thus difficult to sufficiently measure a blocking current derived from each base.

As a translocation control method, there is known a method that includes immobilizing an end of the target DNA to be read on an end of a probe and controlling a minute displacement of the probe using an external drive mechanism (a motor and a piezoelectric element), thereby controlling the movement of the DNA passing through a nanopore. In Non Patent Literature 1 and 2, DNA is immobilized on an end of a probe of an atomic force microscope (AFM) so that the DNA is introduced into a nanopore. DNA is negatively charged in an aqueous solution. Therefore, it is introduced into a nanopore by receiving a force due to a potential difference generated around the nanopore. Herein, since an atomic force microscope is used, DNA is immobilized on an AFM probe. Therefore, a phenomenon that the DNA receives an attractive force from an electric field around the nanopore can be monitored from deflection of the probe that occurs when the AFM probe is pulled by the DNA. At the same time, monitoring an ion current that vertically flows through the nanopore can acquire blocking signals generated when the DNA passes through the nanopore. Since it was confirmed that such signals are synchronized with one another, it was verified that both dsDNA and ssDNA can be introduced into and extracted from the nanopore.

CITATION LIST

Patent Literature

Patent Literature 1: US 2006/0057585 A1

Non Patent Literature

Non Patent Literature 1: Hyun C. et al., 2013 Nano 7, 7, 5892-5900
Non Patent Literature 2: Nelson E. M. et al., 2014 Nano 8, 6, 5484-5493

SUMMARY OF INVENTION

Technical Problem

The aforementioned system has a mechanism in which, after a nanopore is found out by the probe, DNA is introduced into the nanopore. According to such a mechanism, the position of a nanopore with a size of about 1.4 nm, which is formed in a nanopore thin film with a size of greater than or equal to several hundred nm to several ten µm on one side, is searched for. Therefore, the throughput is low. Further, as an atomic force between the nanopore thin film and a cantilever is measured to find out the nanopore, the rigidity of the AFM probe inevitably becomes low. This decreases the precision of the DNA translocation control and becomes a cause for fluctuation of blocking signals in a sequencing analysis after DNA is introduced into the nanopore.

Solution to Problem

In order to solve the aforementioned problems, the present invention proposes a system for translocating a biomolecule using a biomolecule-immobilized probe having a biomolecule-immobilized region with a size of greater than or equal to the size of a thin film with a nanopore. The immobilization density of biomolecules on the biomolecule-immobilized probe is controlled such that at least one biomolecule can enter an electric field region around the nanopore when the biomolecule-immobilized probe has moved close to a nanopore device.

According to such a configuration, it is possible to find out the position of a nanopore out of a large region of a thin film and eliminate the need to perform drive control of the thin film in the in-plane direction when a biomolecule is introduced into the nanopore, and thus increase the measurement throughput. Further, a structure provided with a high-rigidity immobilizing probe is used to increase the precision of the DNA translocation control and achieve single-base resolution.

An exemplary biomolecule measurement system in accordance with the present invention includes a first liquid tank adapted to be filled with an electrolytic solution; a second liquid tank adapted to be filled with the electrolytic solution; a nanopore device adapted to have supported thereon a thin film with a nanopore, the nanopore device being provided between the first liquid tank and the second liquid tank so as to allow the first liquid tank and the second liquid tank to communicate with each other via the nanopore; a biomolecule-immobilized probe that is adapted to be disposed in the first liquid tank, has a larger size than the thin film, and is adapted to have a biomolecule immobilized thereon; a drive mechanism adapted to drive the biomolecule-immobilized probe in a direction toward or away from the thin film; a control unit configured to control the drive mechanism; a first electrode provided in the first liquid tank; a second electrode provided in the second liquid tank; stopping means configured to prevent contact between the biomolecule-immobilized probe and the thin film; a power supply configured to apply a voltage across the first electrode and the second electrode; and a measuring unit configured to measure an ion current flowing between the first electrode and the second electrode. The measuring unit is configured to acquire sequence information on a biomolecule having one end immobilized on the biomolecule-immobilized probe on the basis of an ion current that is measured when the biomolecule passes through the nanopore.

An exemplary biomolecule measurement method in accordance with the present invention includes a step of applying a voltage across a thin film with a nanopore disposed in an electrolytic solution via the nanopore, thereby generating an electric field around the nanopore; a step of driving a biomolecule-immobilized probe in the electrolytic solution in a direction toward the thin film, the biomolecule-immobilized probe having a larger size than the thin film and having a lower surface with a plurality of biomolecules immobilized thereon; a step of stopping drive of the biomolecule-immobilized probe when the biomolecule-immobilized probe has moved close to the thin film by a predetermined distance; a step of confirming that one of the biomolecules has entered the nanopore from a change in ion current that flows through the nanopore; a step of measuring the ion current while driving the biomolecule-immobilized probe in a direction away from the thin film; and a step of acquiring from the measured ion current information to identify a molecule that forms the biomolecule.

Advantageous Effects of Invention

According to the present invention, a biomolecule can be introduced into a nanopore without the need to check the position of the nanopore in a thin film. In addition, displacement stability is ensured and stable acquisition of blocking signals is realized.

Other problems, configurations, and advantageous effects will become apparent from the following description of embodiments.

DESCRIPTION OF EMBODIMENTS

Hereinafter, an embodiment of the present invention will be described with reference to the drawings. A nanopore described in each embodiment is a pore with a nanosize that is provided in a thin film and that penetrates the thin film. The thin film is mainly formed of an inorganic material. Examples of the thin film materials include SiN, $SiO_2$, Graphene, Graphite, and Si, as well as organic materials and polymeric materials. A nanopore thin film with a nanopore is formed on a part of a nanopore device, and has a structure in which the nanopore thin film is supported at its ends on the nanopore device and thus is suspended in the air without having a supporting film above or below the nanopore thin film. Examples of biomolecules as referred to in the present specification include nucleic acids, proteins, amino acids, and long-chain polymers.

Embodiment 1

Figure 1:
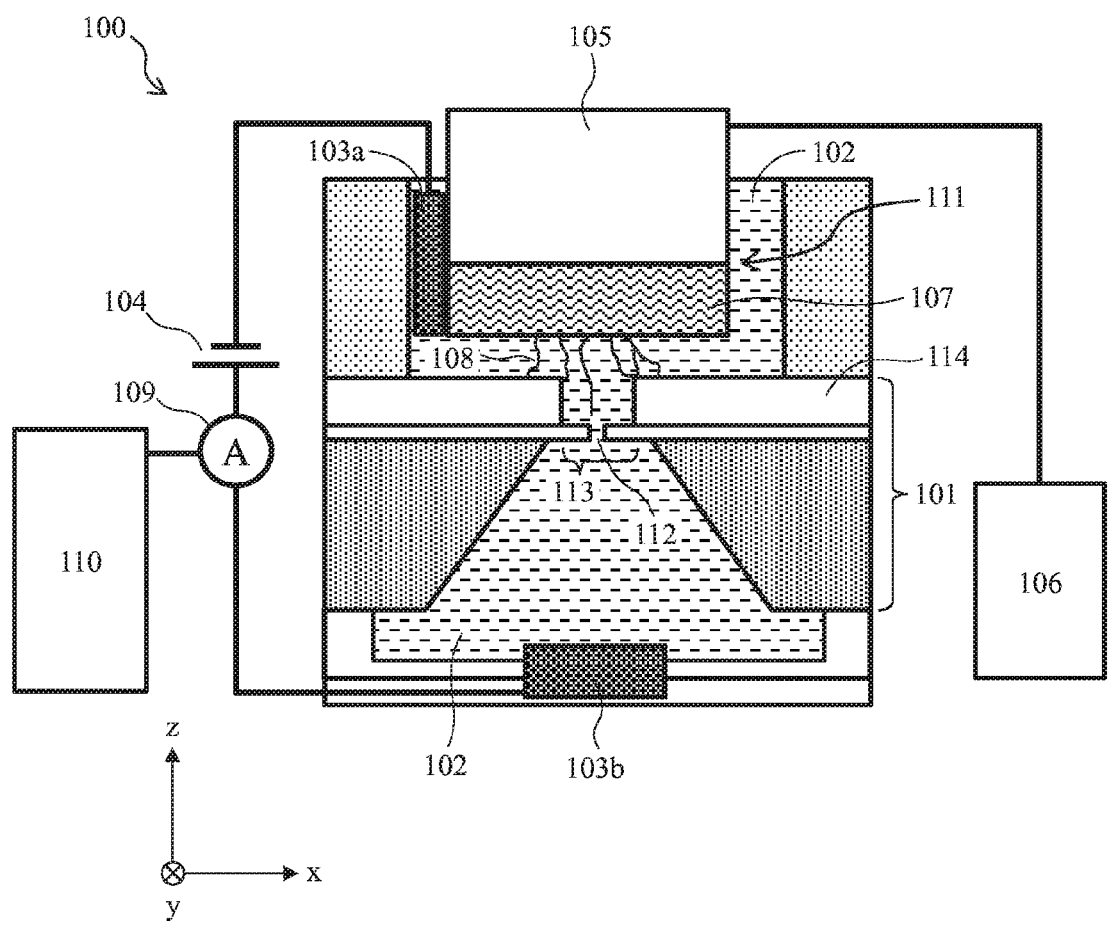
FIG. 1 is a cross-sectional schematic view illustrating an exemplary configuration of a biomolecule measurement system.

A biomolecule measurement system with a translocation control mechanism of the present invention, and an example in which the sequence of a biomolecule is read using the system will be described. FIG. 1 is a cross-sectional schematic view illustrating an exemplary configuration of a biomolecule measurement system.

A biomolecule measurement system 100 in this embodiment includes two, upper and lower liquid tanks separated by a nanopore device 101, and each liquid tank is filled with an electrolytic solution 102. As the electrolytic solution, KCl, NaCl, LiCl, MgCl$_2$, or the like is used. In addition, the solution may also contain mixed therein greater than or equal to 4 M urea to suppress folding of biomolecules. Further, the solution may also contain mixed therein a buffering agent to stabilize biomolecules. As the buffering agent, TE, PBS, or the like is used. The nanopore device 101 has a thin film 113 formed thereon, and a nanopore 112 is formed at any given position in the thin film 113. The two, upper and lower liquid tanks communicate with each other via the nanopore 112 in the thin film 113 that is supported on the nanopore device 101. Ag/AgCl electrodes 103a and 103b are disposed in the two respective liquid tanks so as to be in contact with the electrolytic solution 102, and a power supply 104 and an ammeter 109 are connected between the electrodes 103a and 103b. The ammeter 109 is connected to an ADC and a PC 110, and can record a current value acquired. Meanwhile, the upper liquid tank has disposed therein a drive mechanism 105 that is connected to a drive mechanism control unit 106. A biomolecule-immobilized probe 107 is coupled to the drive mechanism 105 by a connecting unit 111. The biomolecule-immobilized probe 107 has a larger size than the thin film 113, and the lower flat surface of biomolecule-immobilized probe 107 is adapted to have biomolecules 108 immobilized thereon.

When the biomolecule-immobilized probe 107 contacts the thin film 113 with the nanopore 112 formed therein, there is a possibility that the thin film 113 may become damaged. Therefore, stopping means is provided to prevent contact between the biomolecule-immobilized probe 107 and the thin film 113 when the biomolecule-immobilized probe 107 driven by the drive mechanism 105 is lowered toward the nanopore device 101. The stopping means in this embodiment is a space forming film 114 that surrounds the outer side of the thin film 113 of the nanopore device 101 like a bank and forms a space between the biomolecule-immobilized probe 107 and the thin film 113. The thin film 113 with the nanopore 112 is disposed in a circular space formed in the center of the space forming film 114, and the dimension of the thin film 113 is smaller than that of the biomolecule-immobilized probe 107. Thus, the biomolecule-immobilized probe 107 that has moved toward the nanopore device 101 stops upon encountering the space forming film 114 before contacting the thin film 113, and thus will not touch or damage the thin film 113. The dimension of the thin film should be an area with which the thin film strength is obtained and in which two or more holes are unlikely to be formed when a hole is formed with a voltage applied thereto. Therefore, the suitable diameter of the thin film is about 100 to 500 nm, and the suitable thickness of the thin film is about 1 nm with which a nanopore with an effective thickness corresponding to a single base can be formed, in order to achieve single-base resolution of DNA. The suitable thickness of the space forming film is about 200 to 500 nm in order to maintain the thin film strength and considering fluctuation of the biomolecule immobilization height on the surface of the biomolecule-immobilized probe. In this embodiment, the diameter of the thin film 113 is 500 nm and the thickness of the space forming film 114 is 250 nm.

A method for producing a nanopore device and a method for forming a nanopore are already known, and are described in, for example, Itaru Yanagi et al., Sci. Rep. 4, 5000 (2014). In this embodiment, a thin film adapted to have a nanopore formed therein was produced in accordance with the following procedures. First, Si$_3$N$_4$, SiO$_2$, and Si$_3$N$_4$ were deposited to thicknesses of 12 nm, 250 nm, and 100 nm, respectively, on the front surface of an 8-inch Si wafer with a thickness of 725 μm, and Si$_3$N$_4$ was deposited to a thickness of 112 nm on the rear surface. Next, reactive ion etching was applied to an area of 500 nm square of Si$_3$N$_4$ on the uppermost portion of the front surface and to an area of 1038 μm square of Si$_3$N$_4$ on the rear surface. Further, the Si substrate exposed through etching of the rear surface was etched with TMAH (Tetramethylammonium hydroxide). During the Si etching, the front surface of the wafer was covered with a protective film (ProTEK™B3primer and ProTEK™B3, Brewer Science, Inc.) to prevent etching of SiO on the front surface side. After the protective film was removed, the SiO layer exposed in an area of 500 nm square was removed using a BHF solution (HF/NH$_4$F=1/60.8 min). Accordingly, a nanopore device in which thin-film Si$_3$N$_4$ with a thickness of 12 nm is exposed can be obtained. At this stage, a nanopore is not provided in the thin film yet.

A nanopore was formed in the exposed thin film of the nanopore device using a pulse voltage in accordance with the following procedures. Before the nanopore device formed as above was set in a biomolecule measurement system, hydrophilic treatment was applied to the Si$_3$N$_4$ thin film under the conditions of 10 W, 20 sccm, 20 Pa, and 45 sec using Ar/O$_2$ plasma (SAMCO Inc., Japan). Next, after the nanopore device was set in a biomolecule measurement system with a configuration in which two, upper and lower tanks are separated via the nanopore device, the tanks were filled with 1M KCl, 1 mM Tris-10 mM EDTA, and a solution with a pH of 7.5, and then, Ag/AgCl electrodes were introduced into the respective tanks.

Application of a voltage for forming a nanopore as well as measurement of an ion current that flows through the nanopore after the nanopore is formed is conducted between the Ag/AgCl electrodes. The lower tank is referred to as a cis tank; the upper tank is referred to as a trans tank; the voltage $V_{cis}$ on the side of the cis tank electrode was set to 0 V; and the voltage $V_{trans}$ on the side of the trans tank electrode was selected. The selected voltage was applied using a pulse generator (41501B SMU AND Pulse Generator Expander, Agilent Technologies, Inc.). The current value after the application of each pulse was read using a current amplifier (4156B PRECISION SEMICONDUCTOR ANALYZER, Agilent Technologies, Inc.). The processes of applying a voltage for forming a nanopore and reading an ion current were controlled using a self-produced program (Excel VBA or Visual Basic for Applications). As the pulse voltage application conditions, a current value condition (threshold current) acquired in accordance with the diameter of a pore formed in the thin film before the application of a pulse voltage was selected so that the pore diameter was sequentially increased and a target pore diameter was thus obtained. The pore diameter was estimated from an ion current value. Table 1 shows the criteria for selecting the conditions. Herein, the n-th pulse voltage application time is determined by:

$$t_n = 10^{-3+(1/6)(n-1)} - 10^{-3+(1/6)(n-2)} \text{ for } n>2.$$

TABLE 1

| Pore Diameter before Application of Pulse Voltage | Voltage Application Conditions | | |
|---|---|---|---|
| | Without Aperture to 0.7 nm Φ | to 1.4 nm Φ | to 1.5 nm Φ |
| Applied Voltage ($V_{Cis}$) [V] | 10 | 5 | 3 |
| Initial Application Time [s] | 0.001 | 0.01 | 0.001 |
| Threshold Current | 0.1 nA/0.4 V | 0.6 nA/0.1 V | 0.75 nA/0.1 V |

A nanopore can be formed not only through the application of a pulse voltage but also through electron beam irradiation using a TEM (A. J. Storm et al., Nat. Mat. 2 (2003)).

Referring again to FIG. 1, when a voltage is applied to the two, upper and lower liquid tanks from the power supply 104 via the Ag/AgCl electrodes 103a and 103b, an electric field is generated around the nanopore 112, and then, a biomolecule 108 that is negatively charged in the liquid passes through the nanopore 112. Meanwhile, since an end of the biomolecule 108 is immobilized on the biomolecule-immobilized probe 107, the biomolecule-immobilized probe 107 and the drive mechanism 105 are pulled in the direction toward the lower tank via the biomolecule 108 by the electric field.

Herein, in order to accurately read the base sequence of DNA, for example, it is necessary that the displacement of the biomolecule 108 be less than a distance corresponding to the length of a single base, that is, less than 0.34 nm upon occurrence of fluctuation in the output of the drive mechanism and vibration derived from disturbance.

Next, the conditions to satisfy the aforementioned requirements are considered. Provided that the Young's modulus is E, E is represented as follows.

$$E = \frac{F*L}{S*\Delta L} \quad \text{[Equation 1]}$$

Herein, symbol F represents a force applied to the system, symbol S represents the area of the material, symbol L represents the length of the material, and symbol ΔL represents a displacement that occurs upon reception of the applied force. It is known that when a voltage of 1 mV is applied across the two electrodes via the nanopore, a force of 0.24 pN is applied to DNA (Ulrich F. Keyser et al., Nat. Phys. 2, 473-477 (2006)). Since the applied voltage is likely to fluctuate by about 0.1 mV during analysis, it is necessary that a displacement of greater than or equal to 0.34 nm will not occur in that case. Thus, the Young's modulus of each of the biomolecule-immobilized probe 107, the drive mechanism 105, and the connecting unit 111 therefor should be greater than or equal to 0.07 (L/S) [μN/mm²].

It is also important that the measurement system be thermally stable. It is known that a space has a fluctuation of 0.1° C. even when there is no heat source. Therefore, the temperature change vs. the distance between the nanopore device and the biomolecule immobilization substrate calculated from the entire materials used for the system should be less than or equal to 0.34 nm per 0.1° C.

Therefore, a screw or the like made of stainless steel or invar, for example is preferably used for the connecting unit 111. Alternatively, the biomolecule-immobilized probe 107 can be secured to the drive mechanism 105 through vacuum adsorption or crimping. The drive mechanism 105 is formed of a piezoelectric material typified by a piezoelectric element, and can be driven at a speed of greater than or equal to 0.1 nm/s. As the piezoelectric material, barium titanate ($BaTiO_3$), lead zirconate titanate (PZT), zinc oxide (ZnO), or the like is used.

Ends of the biomolecules 108 and the surface of biomolecule-immobilized probe 107 can be bound to each other through covalent binding, ion binding, electrostatic interaction, a magnetic force, or the like. For example, when DNA molecules are immobilized on the surface of biomolecule-immobilized probe 107 through covalent binding, DNA molecules with ends modified with APTES and glutaraldehyde can be immobilized. Since the biomolecule-immobilized probe 107 uses the aforementioned binding, Si or SiO to which APTES is adapted to be bound is used for the probe 107. As another covalent binding method, gold-thiol binding can be used. Specifically, 5' ends of DNA molecules are modified with thiol, and gold is deposited on the surface of the biomolecule-immobilized probe 107. As the other types of metal deposited on the biomolecule-immobilized probe 107, Ag, Pt, or Ti to which thiol can be bound can also be used.

As a method of using ion binding, there is known a method of immobilizing negatively charged biomolecules on a positively charged surface of a biomolecule-immobilized probe by carrying out a process of positively charging the biomolecule-immobilized probe in a solution through surface modification. As the cationic polymers, polyaniline or polylysine is used. When electrostatic interaction is used, DNA molecules with amino-modified ends can be directly immobilized on the surface of the biomolecule-immobilized probe 107 modified with APTES. In addition, as the substrate surface, a nitrocellulose film, a polyvinylidene fluoride film, a nylon film, or a polystyrene substrate is widely used. In particular, a nitrocellulose film is used in the microarray technology. When a magnetic force is used, DNA molecules are immobilized in advance on the surfaces of magnetic beads, for example, by using the aforementioned binding. Further, a magnetic material is used for the biomolecule-immobilized probe 107 so that the DNA-immobilized magnetic beads and the biomolecule-immobilized probe 107 are allowed to interact with each other, thus allowing for suction of the DNA-immobilized magnetic beads due to a magnetic force. As the magnetic material, iron, silicon steel, amorphous magnetic alloy, nanocrystal magnetic alloy, or the like is used.

When proteins or amino acids are measured as biomolecules, it is also possible to allow the proteins or the amino acids to bind to the immobilization substrate using a similar method by modifying specific binding portions thereof. Accordingly, the binding portions in the proteins can be identified and the sequence information on the amino acids can be obtained.

Figure 2:
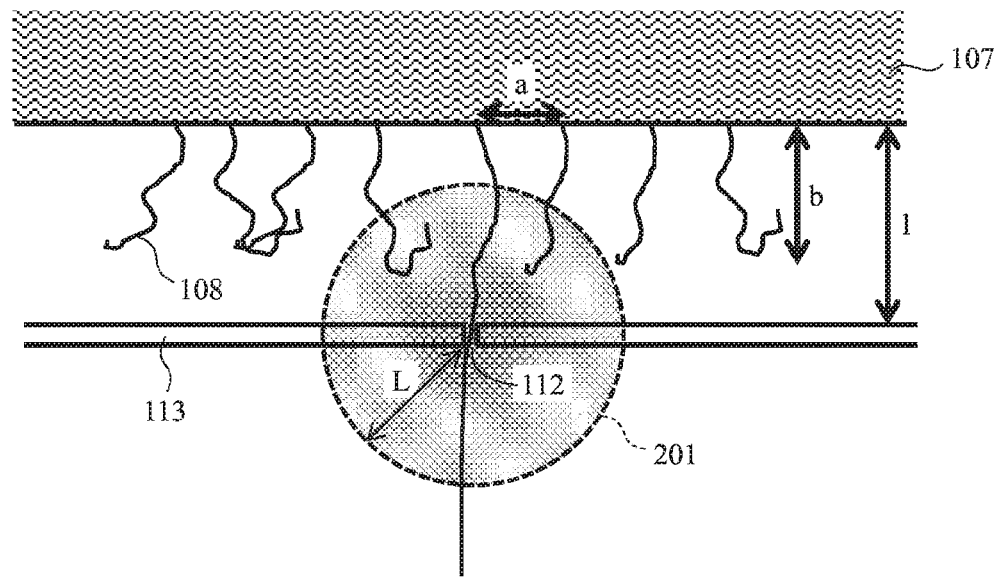
FIG. 2 is a schematic view showing an electric field generated around a nanopore and exemplary introduction of a biomolecule into the nanopore.

The immobilization density of the biomolecules 108 on the biomolecule-immobilized probe 107 is determined by the amount of spread of an electric field formed around the nanopore 112. FIG. 2 is a schematic view showing an electric field generated around the nanopore and exemplary introduction of a biomolecule into the nanopore. As shown in FIG. 2, a potential gradient 201 spreading around the nanopore 112 has the following relationship among the distance L from the nanopore 112, the nanopore diameter d, the thin film thickness t, and the applied voltage ΔV:

$$E(r) = \frac{d^2}{8t} \times \left(\frac{1}{L}\right) \times \Delta V \quad \text{[Equation 2]}$$

For example, when a voltage of 100 mV is applied across a nanopore with a diameter of 1.4 nm formed in a thin film with a thickness of 2.5 nm, an electric field of 0.1 [V/μm] propagates in a region of 100 nm from the nanopore.

Herein, from the electric mobility μ and the diffusion coefficient D of biomolecules, the range in which a biomolecule is confined in the electric field and is introduced into the nanopore is determined. Provided that the range is $L_{diff}$, it is represented by the following equation.

$$L_{diff} = \frac{d^2 \Delta V}{8t} \times \left(\frac{\mu}{D}\right) \quad \text{[Equation 3]}$$

The distance between the biomolecule-immobilized probe 107 and the thin film 113 when the biomolecule-immobilized probe 107 has moved closest to the thin film 113 is indicated by 1. In addition, provided that the effective length of each biomolecule in the solution is b, the biomolecule immobilization pitch a is represented by the following equation.

$$a > \sqrt{L_{diff}^2 - (l - b)^2} \quad \text{[Equation 4]}$$

Figure 3:
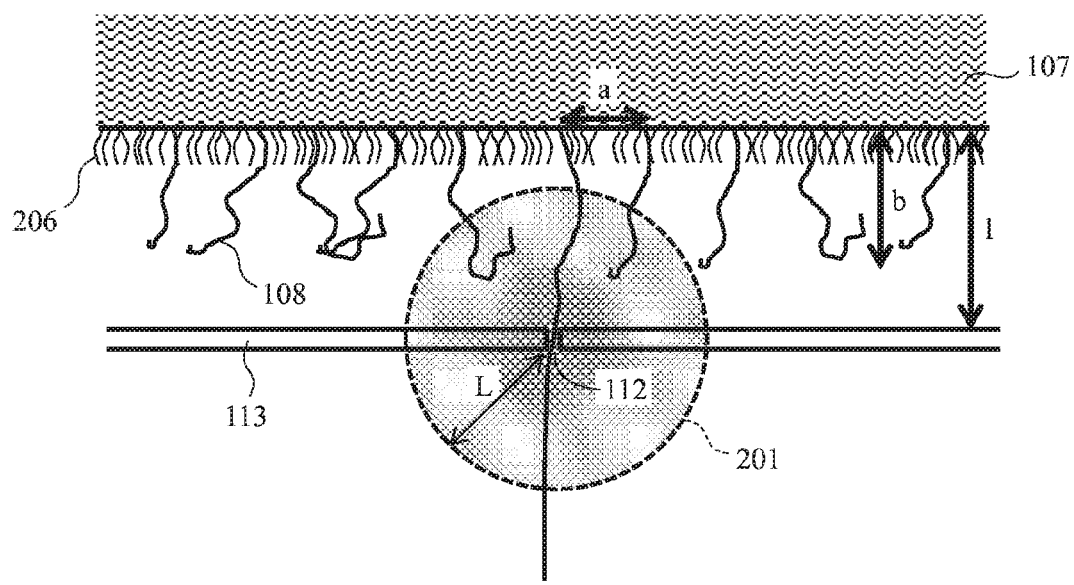
FIG. 3 is a schematic view showing an electric field generated around a nanopore and exemplary introduction of a biomolecule into the nanopore.

In order to realize the above, in immobilizing DNA molecules on the biomolecule-immobilized probe 107, for example, using a DNA solution, which is obtained by mixing short-chain polymers 206 with modified ends in the target DNA molecules, allows the biomolecules (DNA) 108 to be immobilized together with the short-chain polymers 206 with the modified ends as shown in FIG. 3, and thus produce a DNA-immobilized member whose target DNA immobilization density is effectively low. For example, it has been confirmed that when a biomolecule-immobilized probe is prepared using a DNA solution containing 75% 20 mer poly(dA), it is possible to eliminate a phenomenon that a plurality of DNA molecules enter a single pore, by using a nanopore with a pore diameter of 2.5 to 3 nm. That is, it is considered that DNA molecules can be immobilized with a pitch of about 100 nm. The length of each short-chain polymer mixed is not limited to about 2 nm.

Figure 4:
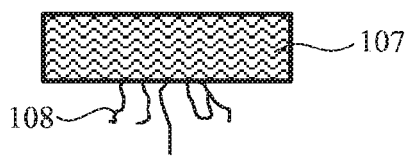
FIGS. 4(a) to 4(c) are schematic views illustrating an example of the procedures for binding biomolecules to a biomolecule-immobilized probe and the procedures for disposing the biomolecule-immobilized probe in a biomolecule measurement system.
Figure 4:
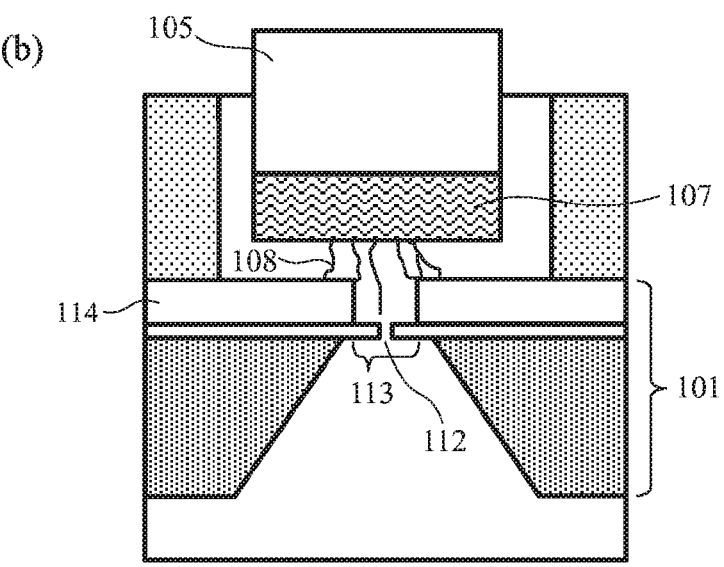
Figure 4:
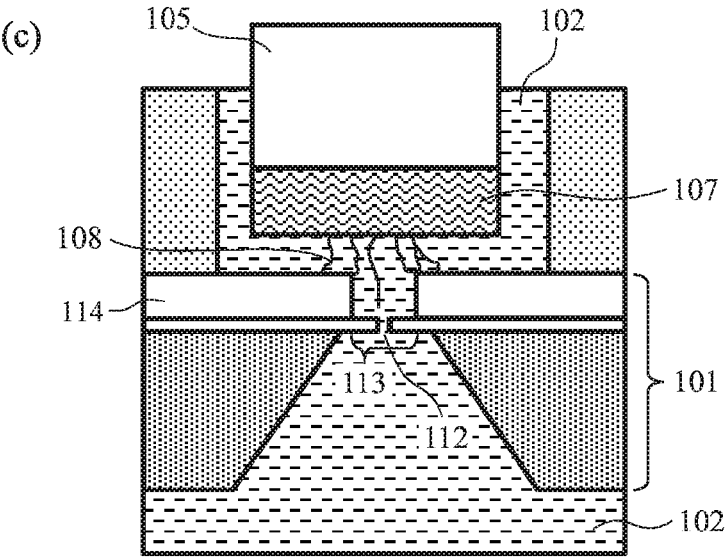

FIGS. 4(a) to 4(c) are schematic views illustrating an example of the procedures for binding biomolecules to the biomolecule-immobilized probe and the procedures for disposing the biomolecule-immobilized probe in a biomolecule measurement system. In the drawings, electrodes are omitted. The preparation steps before measurement shown in FIGS. 4(a) to 4(c) include three steps. In the first step shown in FIG. 4(a), the biomolecules 108 are immobilized on the biomolecule-immobilized probe 107. In the second step shown in FIG. 4(b), the biomolecule-immobilized probe 107 and the drive mechanism 105 are connected together, and are inserted into an upper tank of the biomolecule measurement system. In the third step shown in FIG. 4(c), the electrolytic solution 102 is introduced into spaces above and below the nanopore device 101.

Figure 5:
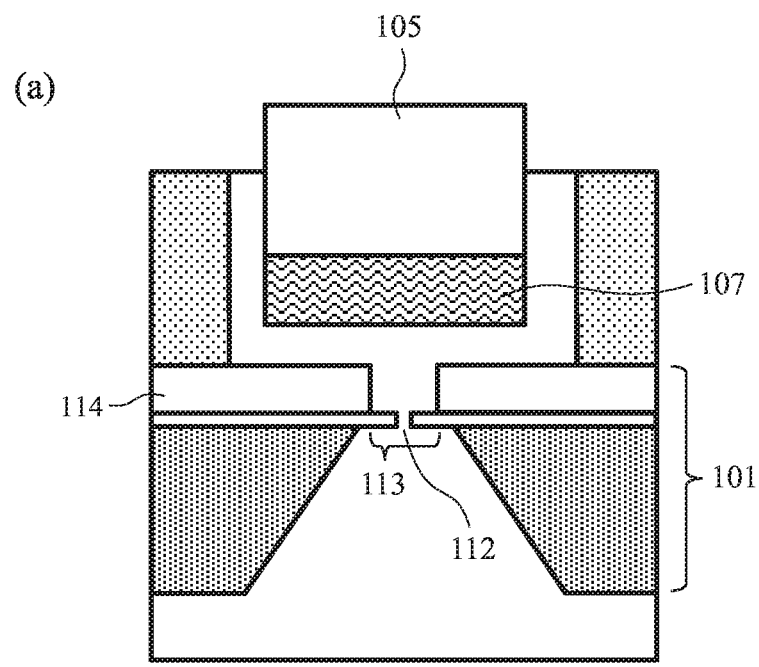
FIGS. 5(a) and 5(b) are schematic views showing another example of the procedures for binding biomolecules to a biomolecule-immobilized probe.
Figure 5:
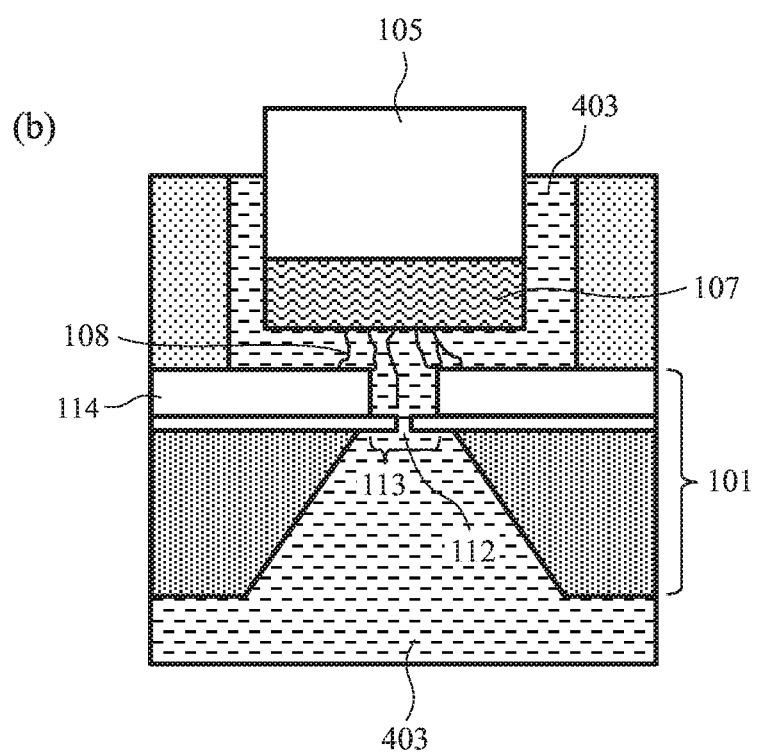

FIGS. 5(a) and 5(b) are schematic views showing another example of the procedures for binding biomolecules to the biomolecule-immobilized probe. In the drawings, electrodes are omitted. The preparation steps before measurement shown in FIGS. 5(a) and 5(b) include two steps. In the first step shown in FIG. 5(a), the biomolecule-immobilized probe 107 is connected to the drive mechanism 105, and is inserted into an upper tank of a biomolecule measurement system. In the second step shown in FIG. 5(b), a biomolecule-mixed electrolytic solution 403 containing dissolved therein the biomolecules 108 in a state in which the biomolecules 108 can bind to the biomolecule-immobilized probe 107 is flowed into the upper and lower tanks of the biomolecule measurement system.

Herein, in order to minimize nonspecific adsorption and increase the density of the intended binding on the surface of the biomolecule-immobilized probe, it is necessary that the surface of the biomolecule-immobilized probe be modified in advance with a binding material for binding biomolecules to the surface of the biomolecule-immobilized probe. The "binding material" herein refers to APTES and glutaraldehyde when biomolecules are to be immobilized using covalent binding via APTES glutaraldehyde, or an organic material on the substrate surface when biomolecules are to be immobilized using ion binding.

When biomolecules are long-chain DNA molecules, strong folding of DNA becomes a problem in a sequence in which a plurality of guanines are sequentially arranged, in particular. If DNA is folded, a phenomenon can occur in which the DNA clogs a region around the nanopore, and thus does not pass through the nanopore, for example. Therefore, it is preferable that an biomolecule-immobilized probe with DNA immobilized thereon be heated in water at a high temperature, in particular, 60 to 98° C. for 10 to 120 minutes, and then quenched to a temperature of 4° C. After that, measurement is performed in a KCl solution at 4° C. or at the room temperature.

Figure 6:
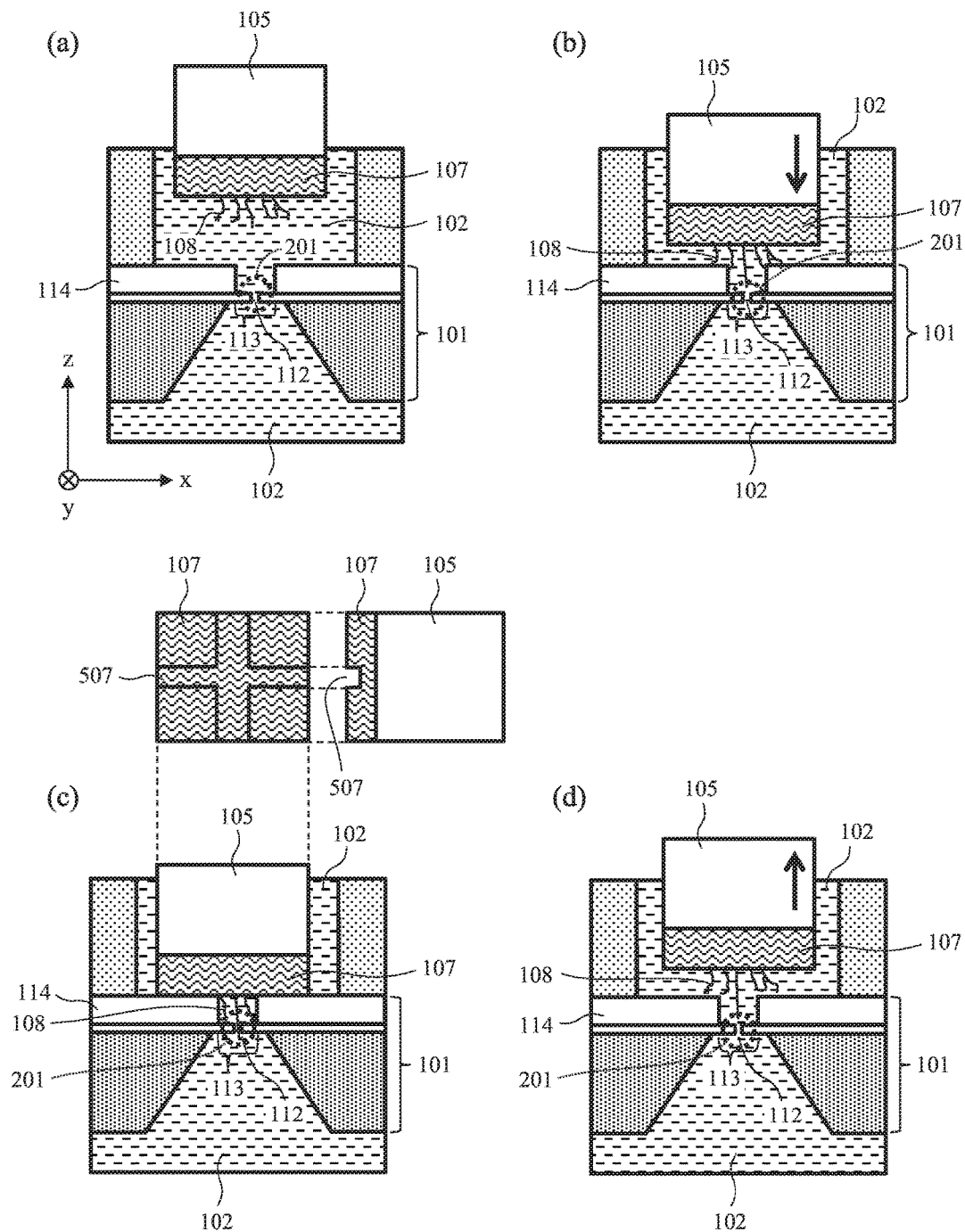
FIGS. 6(a) to 6(d) are schematic views showing the procedures for driving a biomolecule-immobilized probe.

FIGS. 6(a) to 6(d) are schematic views showing the procedures for driving the biomolecule-immobilized probe. In the drawings, electrodes are omitted. The method for driving the biomolecule-immobilized probe herein includes three steps shown in FIGS. 6(a) to 6(d). FIG. 6(a) shows a state in which the biomolecule-immobilized probe 107 with a lower surface to which the biomolecules 108 to be measured have been immobilized in accordance with the procedures shown in FIGS. 4(a) to 4(c) or FIGS. 5(a) and 5(b) is inserted into an upper liquid tank of a biomolecule measurement system, and an electrolytic solution is introduced into the upper and lower liquid tanks, and thus preparation for measurement is ready.

In the first step of driving the biomolecule-immobilized probe shown in FIG. 6(b), the drive mechanism 105 is drive-controlled by the drive mechanism control unit 106 so that the biomolecule-immobilized probe 107 is driven downward along the z-axis and the biomolecule 108 immobilized on the biomolecule-immobilized probe 107 is inserted into the potential gradient 201 generated around the nanopore 112 of the thin film 113. At this time, if the biomolecule 108 has been negatively charged or modified such that it is negatively charged, the biomolecule 108 receives a force from an electric field and attempts to move toward the lower liquid tank through the nanopore 112 from the side of a free end thereof that is not immobilized. The biomolecule 108 thus has a state of being elongated between the portion located within the potential gradient 201 and an end immobilized on the biomolecule-immobilized probe 107 after having passed through the nanopore 112. The fact that the biomolecule has been introduced into the nanopore 112 can be monitored from an ion current.

In the second step shown in FIG. 6(c), the biomolecule-immobilized probe 107 is driven further downward along the z-axis direction by the drive mechanism 105 so that the biomolecule-immobilized probe 107 is allowed to contact the space forming film 114 formed on the nanopore device 101, and the movement of the biomolecule-immobilized probe 107 by the drive mechanism 105 is stopped at that position. As the space forming film 114 is located above the thin film 113, contact between the biomolecule-immobilized probe 107 and the thin film 113 can be avoided and damage to the thin film 113 can thus be prevented. Upon completion of the second step, if there is no biomolecule 108 introduced in the nanopore 112 of the thin film 113, the probability of introduction can be increased by stopping the drive of the drive mechanism 105 for a given period of time. FIG. 6(c) also shows a side schematic view of the drive mechanism 105 and a bottom schematic view of the biomolecule-immobilized probe 107. The lower surface of the biomolecule-immobilized probe 107 is provided with a slit 507 as shown so that a current path is secured between the electrodes disposed in the upper and lower tanks even in a state in which the biomolecule-immobilized probe 107 is in contact with the space forming film 114.

In the third step shown in FIG. 6(d), the drive mechanism 105 is driven in the direction away from the nanopore device 101 by the drive mechanism control unit 106. At this time, the biomolecule 108 is pulled by the biomolecule-immobilized probe 107 and moves upward in the nanopore 112 while being elongated by an electric field. In this period, the sequence of the biomolecule is read from a change in the amount of ion current. The signal value read by the ammeter 109 is amplified as appropriate and is recorded in the PC 110.

Figure 7:
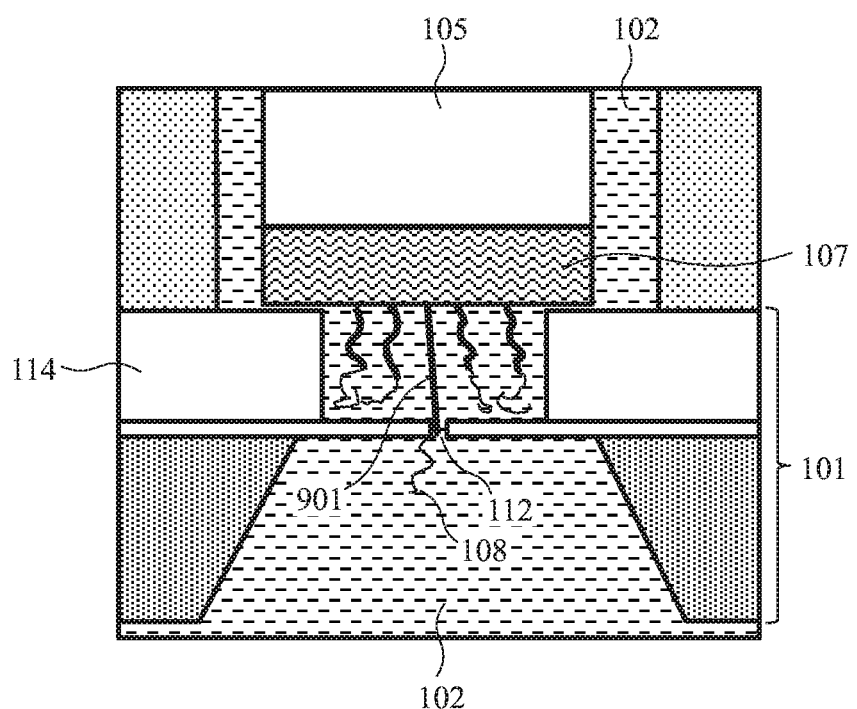
FIG. 7 is a schematic view showing an example in which binding is carried out via a linker.

A time point when the biomolecule-immobilized probe 107 comes into contact with the space forming film 114 in the second step is the analysis start point for analyzing the biomolecule properties in the third step. Thus, of the entire length of the biomolecule, a region of from the immobilized point to the height of the space forming film 114 cannot be analyzed as it does not pass through the nanopore 112. However, as shown in FIG. 7, in immobilizing the biomolecule 108 on the biomolecule-immobilized probe 107, binding the biomolecule 108 to the biomolecule-immobilized probe 107 via a linker 901, which has a length corresponding to the height of the space forming film 114, allows the entire sequence of the biomolecule 108 to be read.

Figure 8:
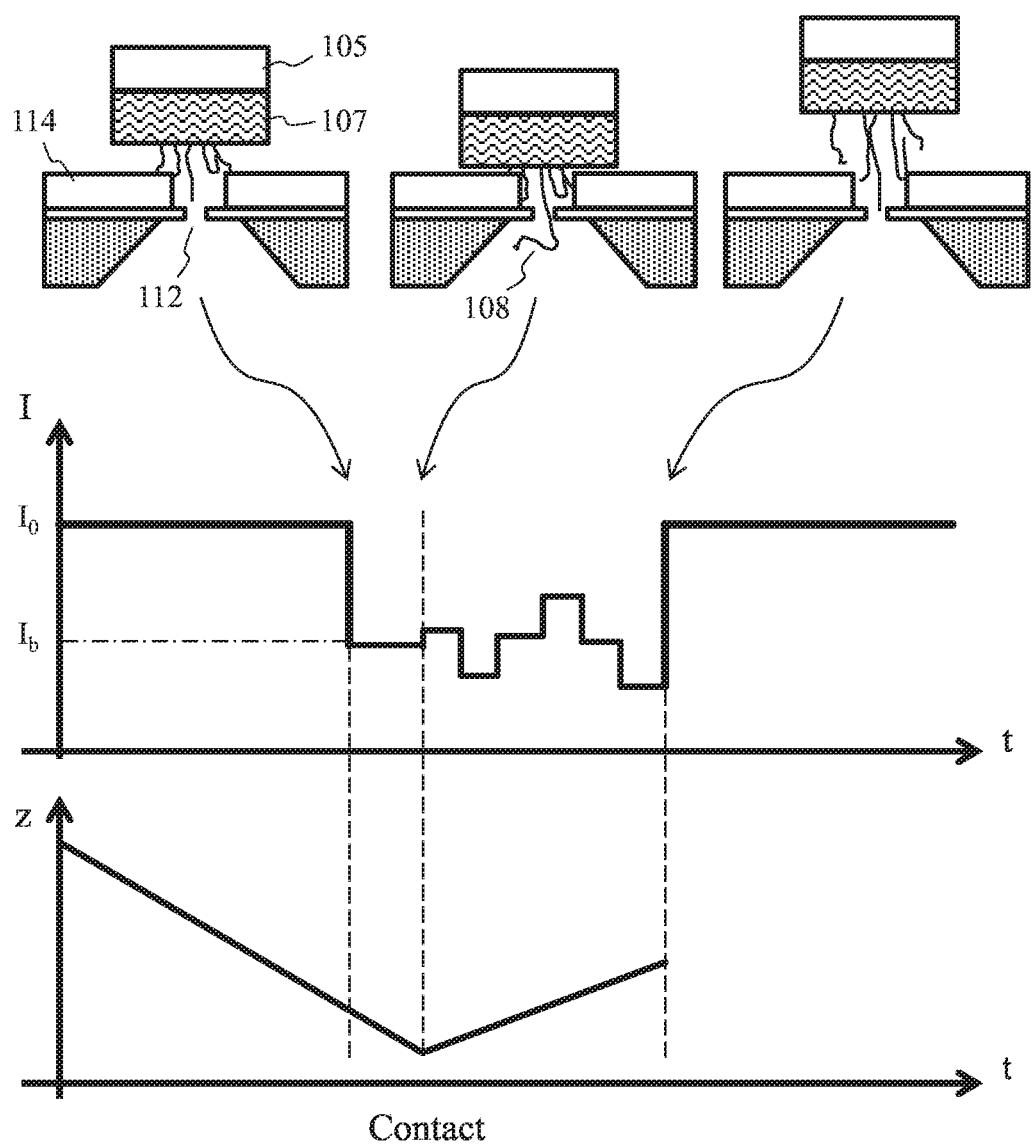
FIG. 8 is a schematic view showing exemplary detection of an ion current signal.

FIG. 8 is a schematic view showing exemplary detection of an ion current signal. A schematic view of the positional relationship of the biomolecule-immobilized probe with respect to the nanopore device is shown in the upper view, a graph of a change in an ion current signal is shown in the middle view, and a graph of a displacement of the drive mechanism is shown in the lower view. The displacement z of the drive mechanism shown in the lower view corresponds to the distance between the nanopore device and the biomolecule-immobilized probe. In addition, the positional relationship between the biomolecule-immobilized probe and the nanopore device, which corresponds to a characteristic point in the ion current signal, is indicated by each arrow.

Referring to FIG. 8, before the biomolecule-immobilized probe 107 moves close to the nanopore device, an ion current signal $I_0$ in accordance with the diameter of the nanopore is obtained. When the biomolecule 108 has entered the nanopore 112, a reduction in the amount of ion current occurs in accordance with the average diameter of the biomolecule. At this time, the speed at which the biomolecule passes through the nanopore is not the driving speed of the biomolecule-immobilized probe but the speed of the free electrophoresis of the biomolecule. This is because when a biomolecule has entered an electric field from outside of the electric field, the biomolecule is folded and deflected and thus is not influenced by an end thereof that is immobilized on the biomolecule-immobilized probe. At this time, the measurement resolution is not obtained, and the acquired ion current value shows the average current value $I_b$ dependent on the average diameter of the biomolecule.

After the biomolecule-immobilized probe 107 has contacted the space forming film 114 of the nanopore device, the translocation speed of the biomolecule that is pulled upward by the drive mechanism 105 becomes equal to the movement speed of the biomolecule-immobilized probe 107. Therefore, the biomolecule can be translocated at a speed that is necessary to obtain the property resolution. For example, in order to measure the difference between the types of individual bases contained in a DNA strand on the basis of the amounts of blocking currents, it is considered that the speed of the DNA passing through the nanopore should be set to greater than or equal to 100 μs per base in view of current noise generated during measurement and a time constant of fluctuation of DNA molecules. Thus, controlling the drive mechanism 105 to move the biomolecule-immobilized probe 107 upward at a speed of less than 100 μs per base can obtain a signal that reflects the base sequence of the biomolecule. Meanwhile, as the analysis throughput should be maintained high, the movement speed is desirably not slower than 10 ms per base. That is, the drive mechanism preferably drives the biomolecule-immobilized probe at a speed of 34 nm/sec to 34 μm/sec.

Herein, the method of acquiring data on the sequence of a biomolecule is not limited to acquiring a change in the amount of ion current. When an electrode for tunnel current is formed above the nanopore device and a nanopore is formed around the electrode, the sequence of a biomolecule can be analyzed from a change in the amount of tunnel current (Makusu Tsutsui et at, Nat. Nanotechnol. 5, 286-290 (2010)). Meanwhile, when a nanopore is formed in a FET device, a sequence can be analyzed from a change in the amount of electric charge. Alternatively, analysis that uses light is also possible. In such a case, the sequence of a biomolecule can be analyzed from the amount of absorption, the amount of reflection, light emission wavelength, and the like (Ping Xie et al., Nat. Nanotechnol. 7, 119-125 (2012)). In the present invention, a biomolecule that moves through the nanopore 112 can also be analyzed using any of such known methods instead of using an ion current.

Figure 9:
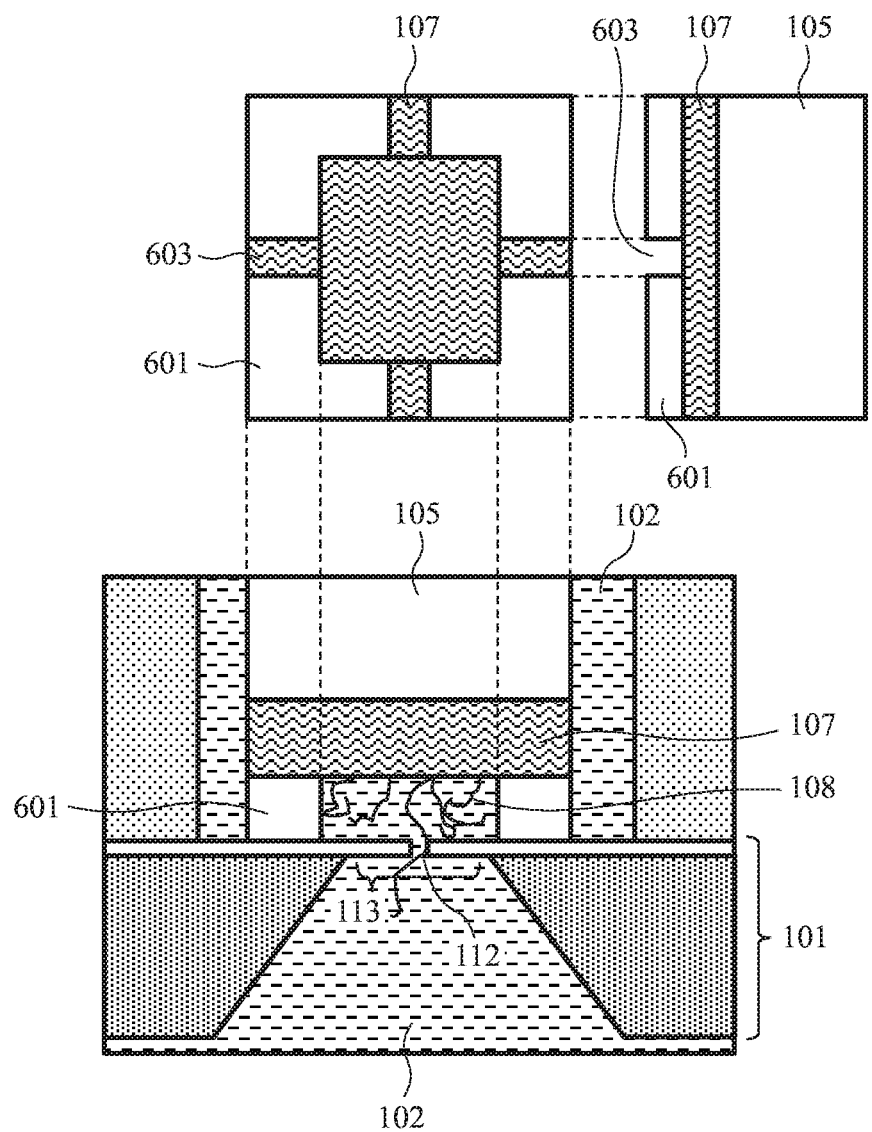
FIG. 9 is a schematic view showing an exemplary stopping means.

FIG. 9 is a schematic view showing another exemplary stopping means that prevents contact between the biomolecule-immobilized probe and the thin film. FIG. 9 also shows a side schematic view of the biomolecule-immobilized probe 107 including the drive mechanism 105 and a bottom view having a slit 603. In this example, a space forming film 601 was machined such that it protruded downward from the lower surface of the biomolecule-immobilized probe 107 and not formed directly on the nanopore device 101. The space forming film 601 is formed on the outer circumference, four corners, or opposite two sides of the lower surface of the biomolecule-immobilized probe 107 such that the space forming film 601 contacts the nanopore device 101 at a position outside the thin film 113. That is, the space forming film 601 is provided on at least a part of a region outside a portion, which is opposite the thin film 113, of the lower surface of the biomolecule-immobilized probe 107. When the biomolecule-immobilized probe 107 moves in the direction toward the nanopore device 101, a space is formed between the biomolecule-immobilized probe 107 and the thin film 113 by the space forming film 601 so that damage to the thin film 113 upon contacting the biomolecule-immobilized probe 107 is prevented.

Figure 10:
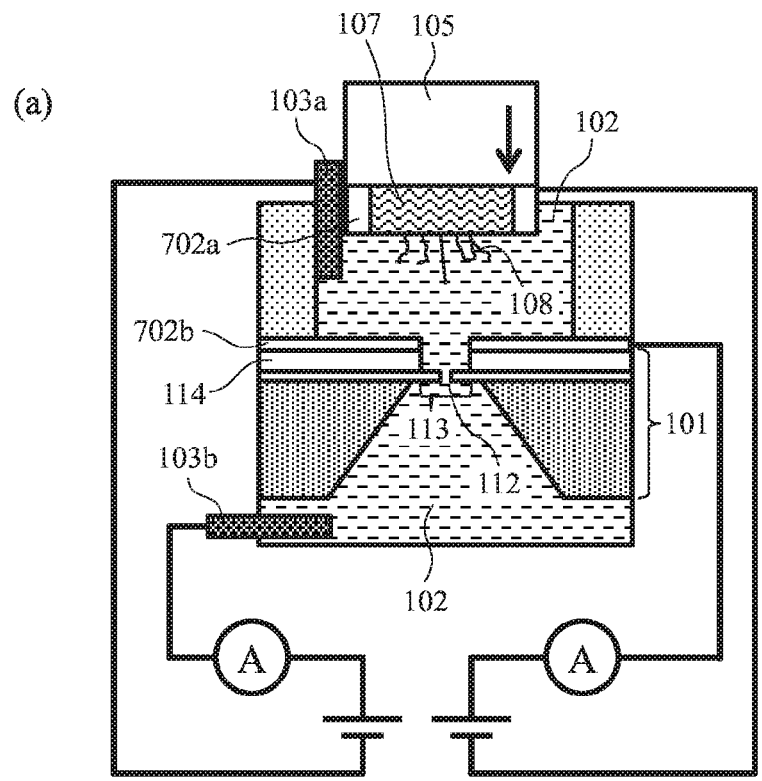
FIGS. 10(a) and 10(b) are schematic views showing an exemplary stopping means.
Figure 10:
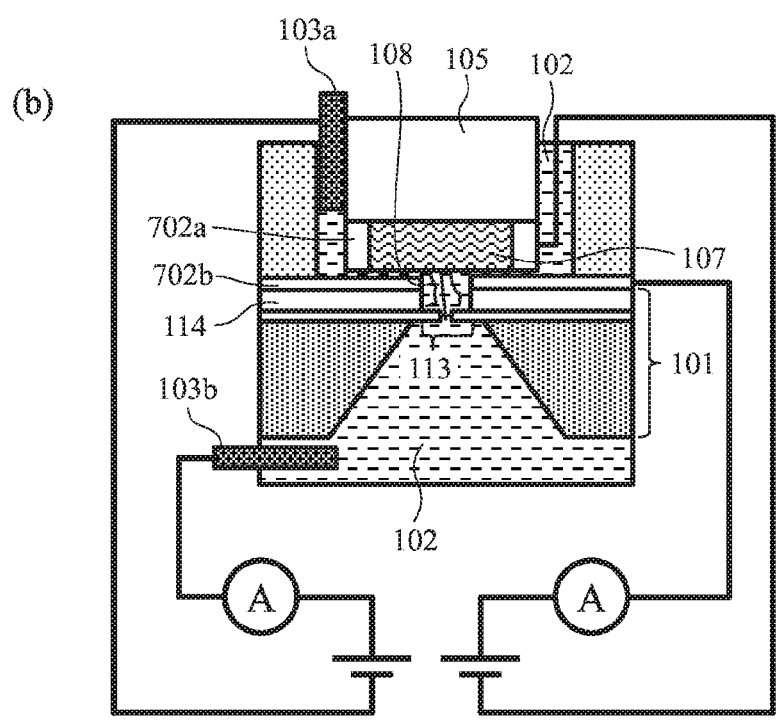

FIGS. 10(a) and 10(b) are schematic views showing another exemplary stopping means that prevents contact between the biomolecule-immobilized probe and the thin film. FIG. 10(a) shows a state before the biomolecule-immobilized probe contacts the nanopore device, and FIG. 10(b) shows a state after the biomolecule-immobilized probe has contacted the nanopore device. It is acceptable as long as the stopping means can form a space for avoiding contact between the biomolecule-immobilized probe 107 and the thin film 113. As the stopping means in this example, electrodes 702a and 702b are arranged on a part of the upper surface of the nanopore device 101 and a part of a region outside a portion, which corresponds to the thin film, of the lower surface of the biomolecule-immobilized probe 107, respectively so that the relative distance between the biomolecule-immobilized probe 107 and the nanopore device 101 is detected from a change in the capacitance between the electrodes 702a and 702b and contact therebetween is monitored. The voltage applied across the electrodes 702a and 702b is selected in accordance with a predicted amount of current and the measured current. In addition, the voltage can be measured by applying a pulse voltage in order to prevent corrosion and oxidation of the electrodes. The biomolecule-immobilized probe 107 is driven in the direction toward the nanopore device 101, and the distance between the nanopore device 101 and the biomolecule-immobilized probe 107 is detected from a change in a signal acquired from the electrodes 702a and 702b when the nanopore device 101 and the biomolecule-immobilized probe 107 have approached close to each other, and the drive of the drive mechanism 105 is stopped. Instead of acquiring a signal indicating a change in the capacitance, it is also possible to monitor a contact from short. While a voltage is applied across the electrodes 702a and 702b that form the stopping means, no voltage is applied across the measurement electrodes 103a and 103b.

Figure 11:
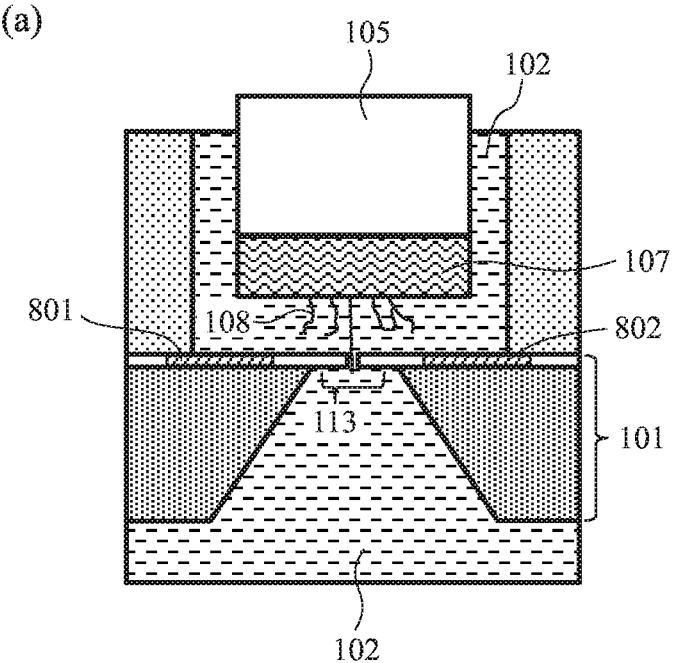
FIGS. 11(a) and 11(b) are schematic views showing an exemplary stopping means.
Figure 11:
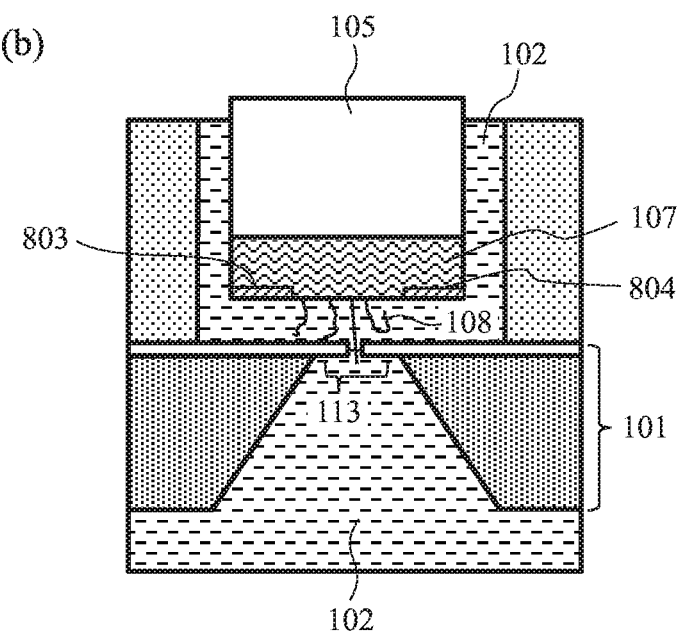

FIGS. 11(a) and 11(b) are schematic views showing another exemplary stopping means that prevents contact between the biomolecule-immobilized probe and the thin film. In the example shown in FIG. 11(a), electrodes 801 and 802 are disposed only on the nanopore device 101 and are wired so that the relative distance between the biomolecule-immobilized probe 107 and the nanopore device 101 is detected from a change in the amount of current when the biomolecule-immobilized probe 107 has moved close to the nanopore device 101. The electrodes 801 and 802 are arranged on the outer circumference, four corners, or opposite two sides of a region outside the thin film 113 on the upper surface of the nanopore device 101. In the example shown in FIG. 11(b), electrodes 803 and 804 are disposed on the lower surface of the biomolecule-immobilized probe 107 and are wired so that the relative distance between the biomolecule-immobilized probe 107 and the nanopore device 101 is detected based on a similar mechanism. It is acceptable as long as the electrodes 803 and 804 are disposed on four corners or opposite two sides of a region outside a portion, which corresponds to the thin film 113, of the lower surface of the biomolecule-immobilized probe 107.

When four electrodes are arranged on four corners, respectively, such electrodes can also be used to obtain a balanced output of the biomolecule-immobilized probe 107.

In such a case, the drive mechanism 105 is provided with a tilt adjustment function to adjust a tilt of the drive mechanism 105 so that current values acquired from the four points become substantially identical. For example, four independent goniometers are provided at the four corners, and the goniometers are adjusted manually or automatically on the basis of the amounts of currents acquired from the four portions.

Figure 12:
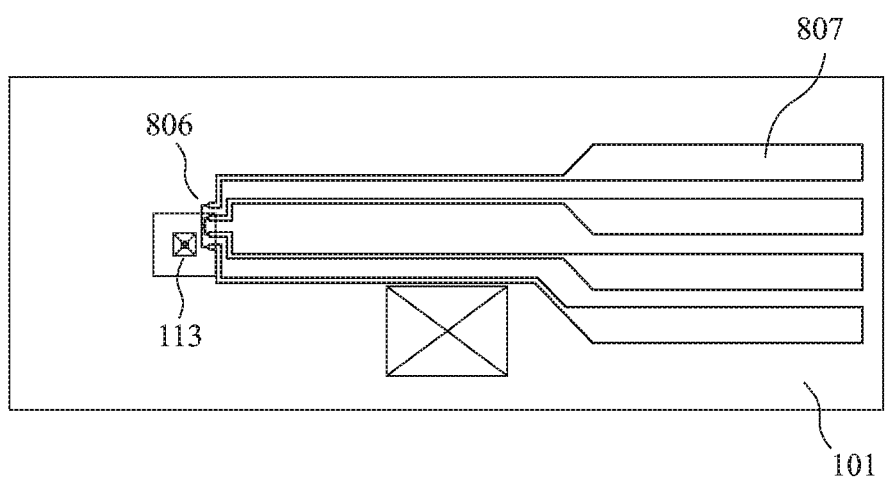
FIGS. 12(a) to 12(c) are top schematic views showing an exemplary arrangement of electrodes on a nanopore device.
Figure 12:
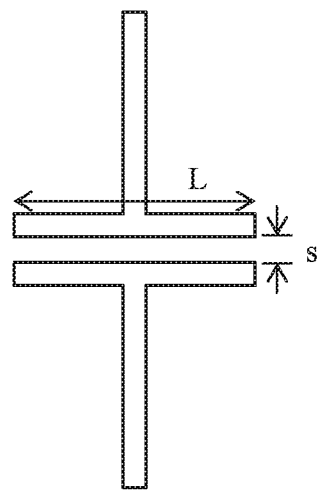
Figure 12:
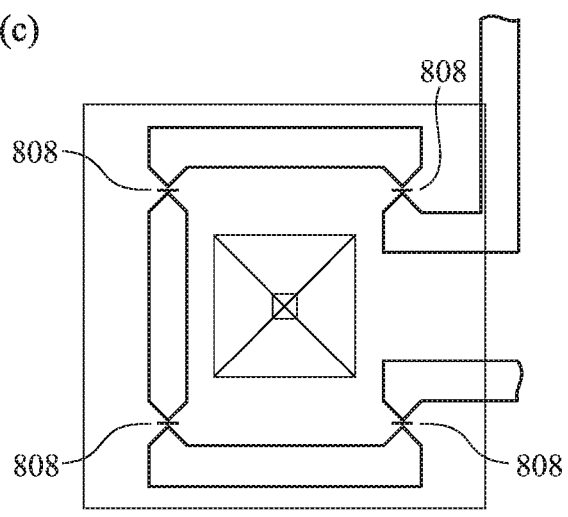

FIGS. 12(a) to 12(c) are top schematic views showing an exemplary arrangement of the electrodes on the nanopore device 101 shown in FIG. 11(a). FIG. 12(a) is a layout of the thin film 113, a sensor wire 806, and an electrode leading wire 807 on the nanopore device 101. FIGS. 12(b) and 12(c) are enlarged views of the sensor wire; specifically, FIG. 12(b) shows an exemplary type of counter electrodes and FIG. 12(c) shows an example in which counter electrodes 808 are arranged in a ring shape at four corners in the peripheral portion of the thin film 113. Herein, a voltage of 1 V was applied across the electrodes shown in FIG. 12(b) each designed to have an electrode length L of 10 μm and an electrode gap s of 0.4 to 2 μm, and then, a change in the amount of current flowing between the electrodes when the biomolecule-immobilized probe 107 was moved close to the nanopore device 101 was monitored.

Figure 13:
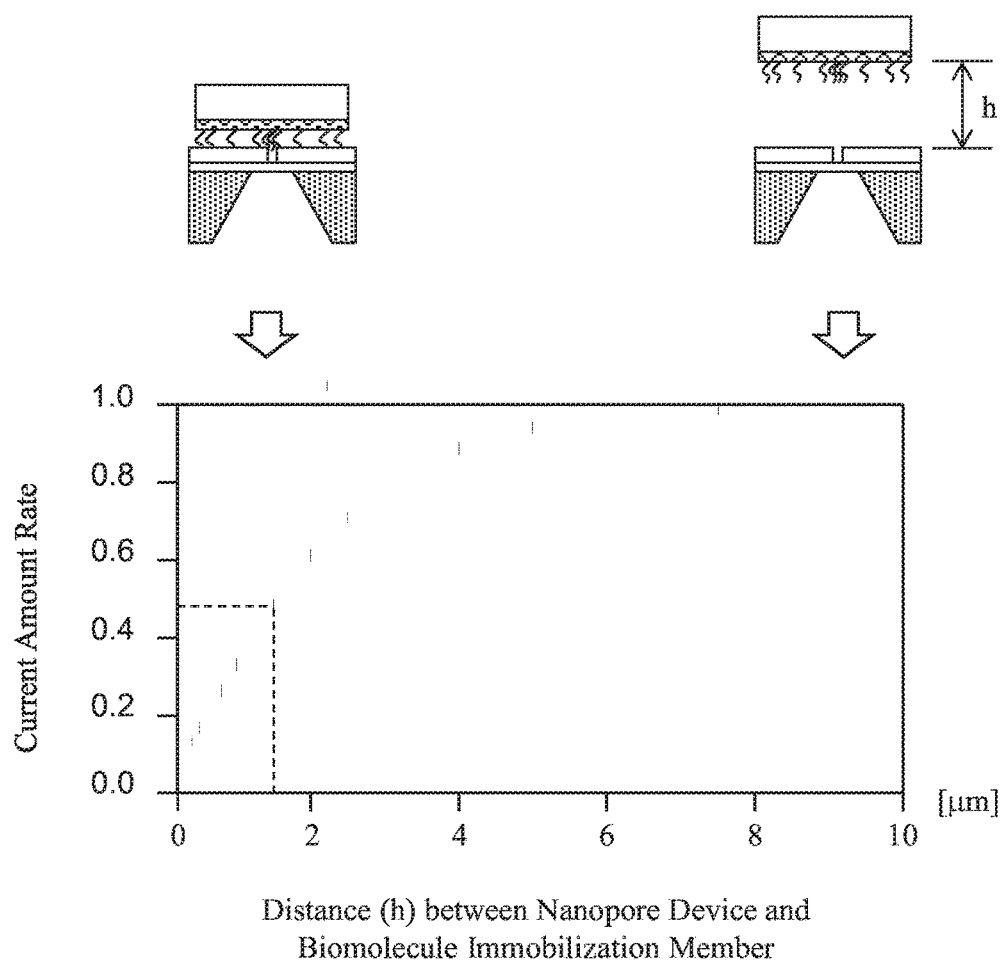
FIG. 13 is a graph showing the relationship between the distance h between a biomolecule-immobilized probe and a nanopore device, and the amount of current.

FIG. 13 is a graph showing the relationship between the amount of current and the distance h between the biomolecule-immobilized probe and the nanopore device that has been normalized from the amount of current that flows when the distance h is 10 μm. As shown in FIG. 13, it was found that when the distance between the biomolecule-immobilized probe and the nanopore device is greater than or equal to 7 μm, the amount of current has almost no dependence on the distance h, but when the distance is less than 7 μm, there is a correlation between the distance and the amount of a reduction in current. Thus, acquiring such a correlation between the distance h and the amount of current can adjust the height of the biomolecule-immobilized probe.

As another example of a method for driving the biomolecule-immobilized probe, there is also known a method of allowing the biomolecule 108 on the biomolecule-immobilized probe 107 to approach a region around a nanopore while elongating the biomolecule 108 in advance. FIGS. 14(a) to 14(d) and FIGS. 15(a) and 15(b) are cross-sectional schematic views each showing an exemplary method for driving the biomolecule-immobilized probe using a biomolecule measurement system with a mechanism for elongating a biomolecule in advance.

Figure 14:
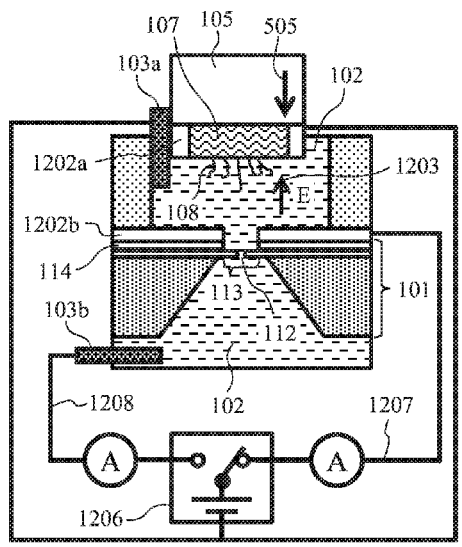
FIGS. 14(a) to 14(d) are cross-sectional schematic views showing an exemplary biomolecule measurement system with a mechanism for elongating a biomolecule in advance.
Figure 14:
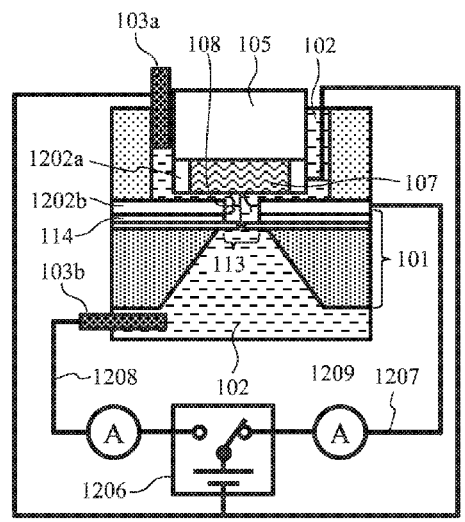
Figure 14:
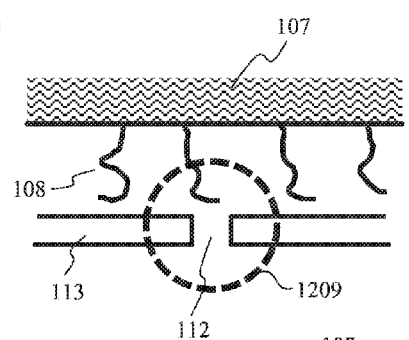
Figure 14:
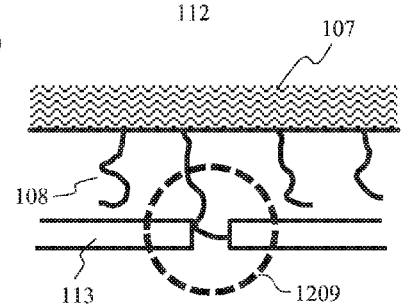

As shown in FIG. 14(a), the biomolecule measurement system in this example includes electrodes 1202a and 1202b on the biomolecule-immobilized probe 107 and the nanopore device 101, respectively. First, a power supply is connected to a circuit 1207, which is connected to the electrodes 1202a and 1202b, by a switching unit 1206 so that a potential gradient 1203 is formed between the biomolecule-immobilized probe 107 and the nanopore device 101. Then, a negatively charged biomolecule 108 is elongated between the biomolecule-immobilized probe 107 and the nanopore device 101 by the potential gradient 1203.

Next, as shown in FIG. 14(b), the drive mechanism 105 is driven so that the biomolecule-immobilized probe 107 is driven downward until it contacts the space forming film 114 on the nanopore device 101. At this time, as shown in an enlarged view of FIG. 14(c), the biomolecule 108 is put in the range of a predicted electric field 1209 that should be generated around the nanopore when the power supply is connected to a circuit 1208 connecting to the electrodes 103a and 103b.

Figure 15:
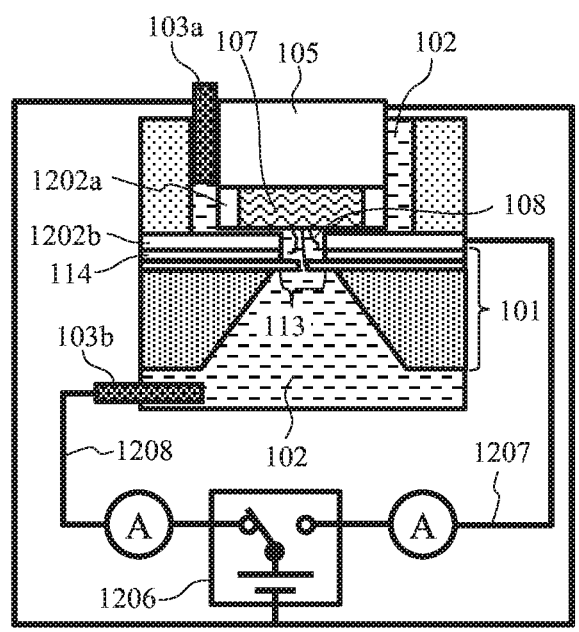
FIGS. 15(a) and 15(b) are cross-sectional schematic views showing an exemplary biomolecule measurement system with a mechanism for elongating a biomolecule in advance.
Figure 15:
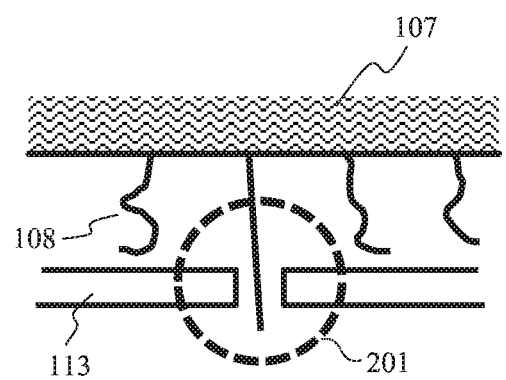

Next, as shown in FIG. 15(a), when the biomolecule-immobilized probe 107 contacts the space forming film 114 on the nanopore device 101, the connection target of the power supply is switched from the circuit 1207 connected to the electrodes 1202a and 1202b to the circuit 1208 that forms an electric field around the nanopore. As shown in FIG. 15(b), a potential gradient 201 is formed around the nanopore, whereby an end of the biomolecule is inserted into the nanopore.

After the step shown in FIG. 14(b), there are cases where an end of a biomolecule does not enter the nanopore and an end of a biomolecule enters the nanopore, though its probability is low, as shown in an enlarged view of FIG. 14(d). The base of a biomolecule can be read from an end thereof only when the end has not entered the nanopore but has entered the region of an electric field.

Figure 16:
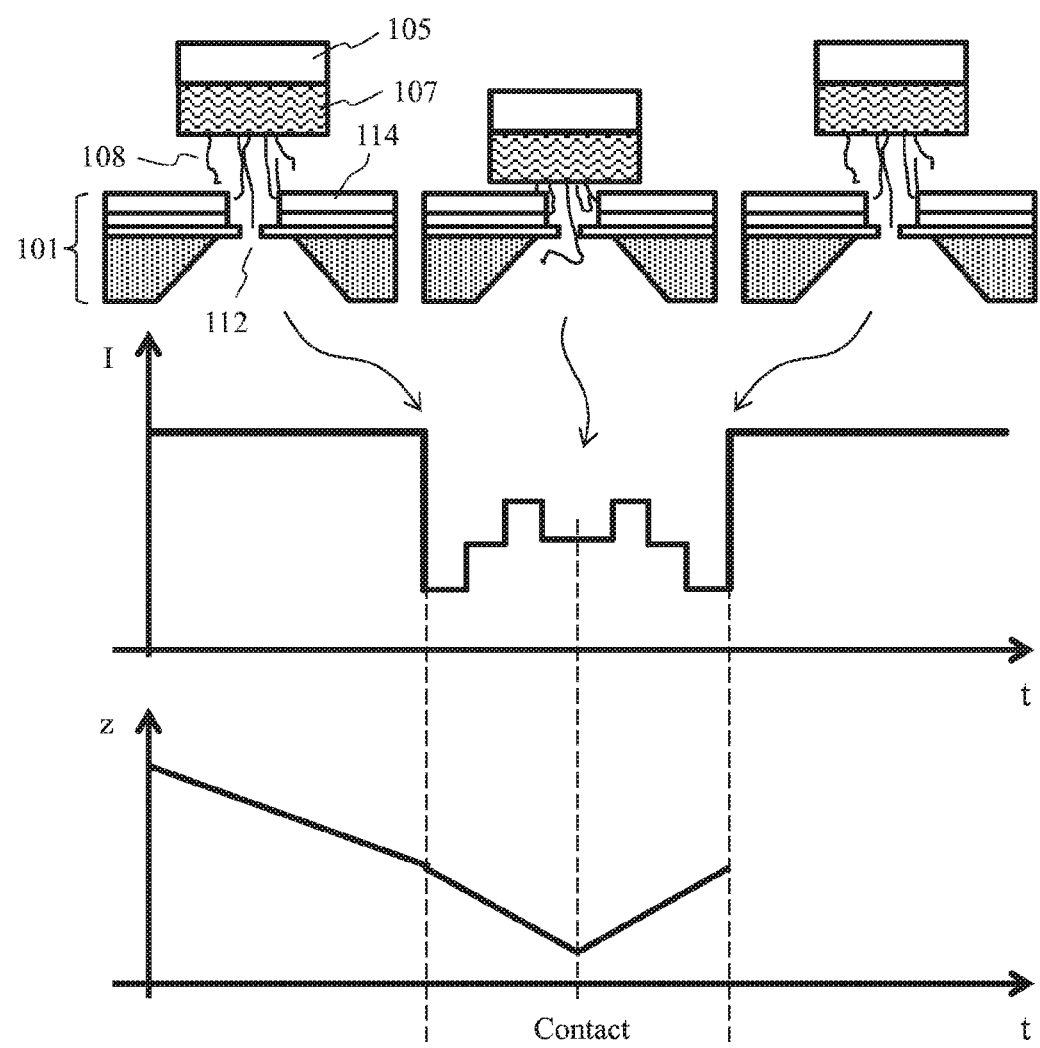
FIG. 16 is a schematic view showing an exemplary signal read from an end of a biomolecule.

FIG. 16 is a schematic view showing an exemplary signal read from an end of a biomolecule. A graph of a change in an ion current signal is shown in the middle view, and a graph of a displacement of the drive mechanism is shown in the lower view. The displacement z of the drive mechanism shown in the lower view corresponds to the distance between the nanopore device and the biomolecule-immobilized probe. In addition, regarding a characteristic point in the ion current signal, the correspondence between the biomolecule-immobilized probe and the nanopore device shown in the upper view is indicated by each arrow.

Before the biomolecule-immobilized probe moves close to the nanopore device, an ion current signal $I_0$ in accordance with the diameter of the nanopore is obtained. When a power supply is connected to the electrodes 103a and 103b to form a potential gradient 201 around the nanopore, an end of the biomolecule 108 is located within the potential gradient 201. Therefore, if the drive mechanism 105 is driven downward along the z-axis, the biomolecule 108 is sequentially introduced into the nanopore 112 from the side of a free end thereof. At this time, as the biomolecule 108 is not deflected, the biomolecule is driven at a speed preset by the drive mechanism control unit 106, and thus, property analysis in accordance with the sequence of the biomolecule becomes possible. Thus, as shown in FIG. 16, a signal read after the biomolecule 108 is introduced into the nanopore 112 and until the biomolecule-immobilized probe 107 contacts the nanopore device 101, and a signal read after the drive mechanism 105 starts to be driven upward along the z-axis and until an end of the biomolecule comes out of the nanopore 112 are symmetrical about the contact time.

Figure 17:
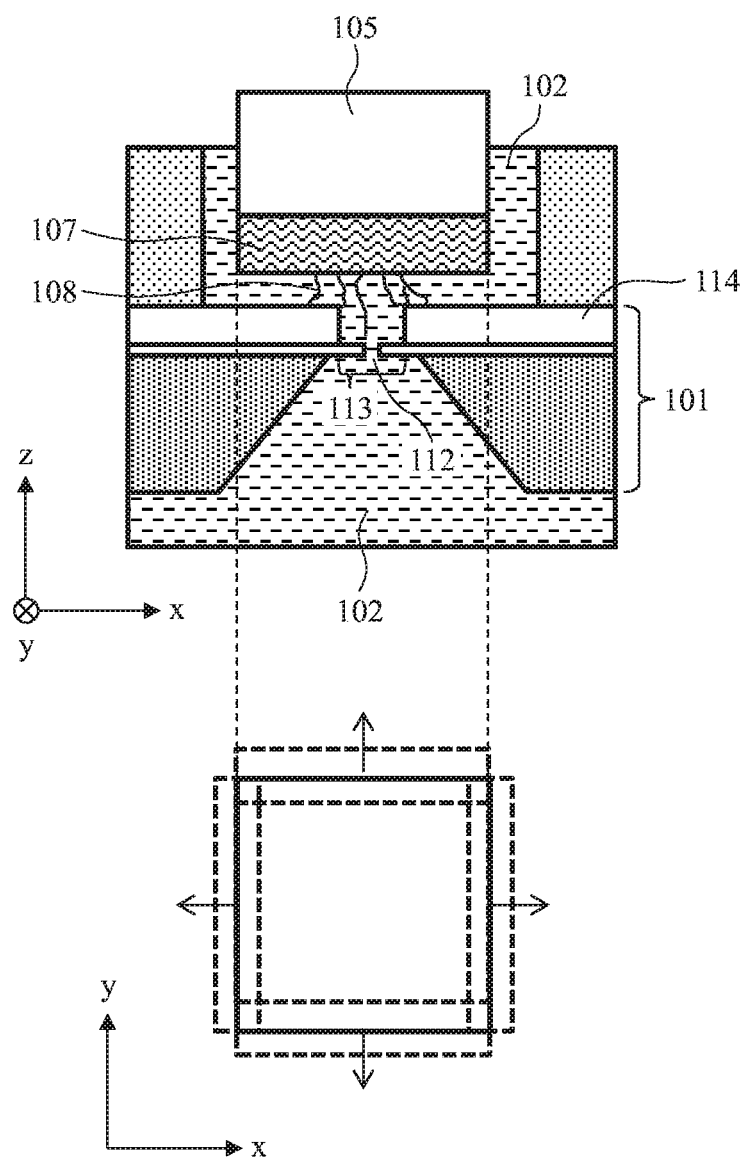
FIG. 17 is a partial cross-sectional schematic view of a biomolecule measurement system and a top schematic view of a drive mechanism.

Of the biomolecules immobilized on the biomolecule-immobilized probe 107, a biomolecule that differs from the initially measured biomolecule can be read by driving the drive mechanism 105 in the x-y directions. FIG. 17 is a partial cross-sectional schematic view of the biomolecule measurement system and a top schematic view of the drive mechanism 105. As shown in the top schematic view, driving the drive mechanism 105 in the x-y directions, that is, in the direction parallel with the plane of the thin film 113 allows another biomolecule to pass through the nanopore 112, thereby realizing analysis of a plurality of biomolecules on the biomolecule-immobilized probe 107.

Figure 18:
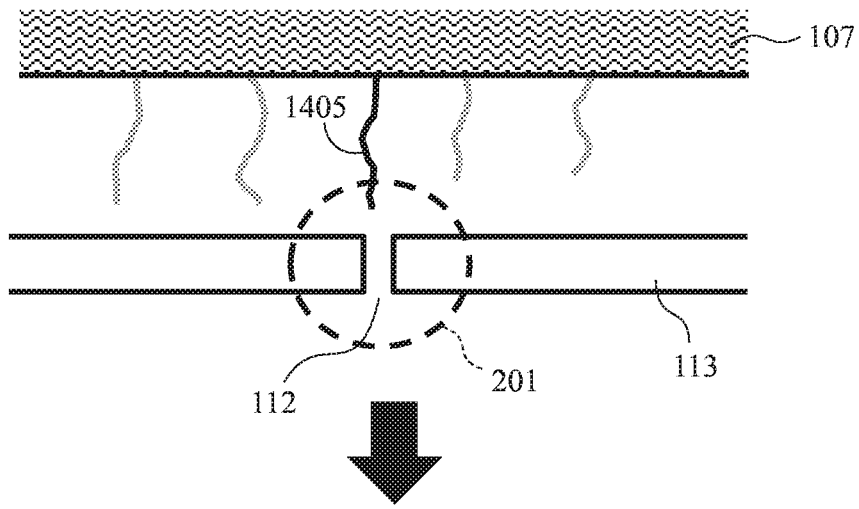
FIGS. 18(a) and 18(b) are enlarged views of a region around a nanopore.
Figure 18:
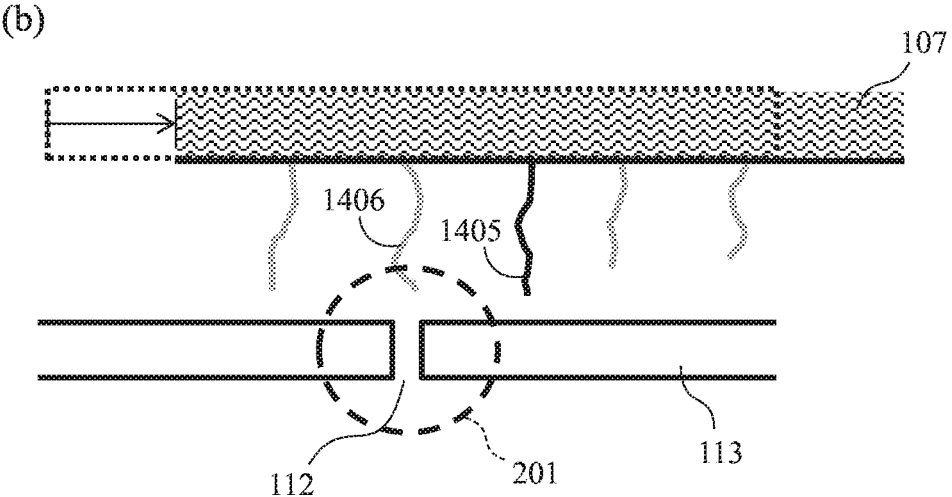

The conditions for realizing analysis of a plurality of biomolecules will be described using enlarged views of a region around the nanopore shown in FIGS. 18(a) and 18(b). FIG. 18(a) is a cross-sectional schematic view showing the positional relationship between the thin film 113 with the nanopore 112 and the biomolecule-immobilized probe 107 when the properties of a first biomolecule 1405 are analyzed. Herein, when a second biomolecule 1406 is analyzed, the biomolecule-immobilized probe 107 is moved in parallel with the plane of the nanopore thin film 113 by the drive mechanism 105 by the same distance as the diameter of the potential gradient 201. FIG. 18(b) is a cross-sectional schematic view showing the positional relationship between the thin film 113 with the nanopore 112 and the biomolecule-immobilized probe 107 after it has been moved. By the movement, a state in which the first biomolecule 1405 will never enter the range of the potential gradient 201 can be created. After that, the biomolecule-immobilized probe 107 is driven toward the thin film 113 by the drive mechanism 105, whereby the second biomolecule 1406 can be introduced into the nanopore 112 and thus analyzed.

Embodiment 2

Hereinafter, an embodiment of the procedures for measuring a biomolecule using a biomolecule measurement system of the present invention will be described. In all of the following steps, an ion current I that flows through a nanopore is measured through an amplifier. In addition, a constant voltage is applied across a pair of Ag/AgCl electrodes inserted into the two respective upper and lower liquid tanks so that an ion current amount $I_0$ in accordance with the size of the nanopore is acquired.

Figure 19:
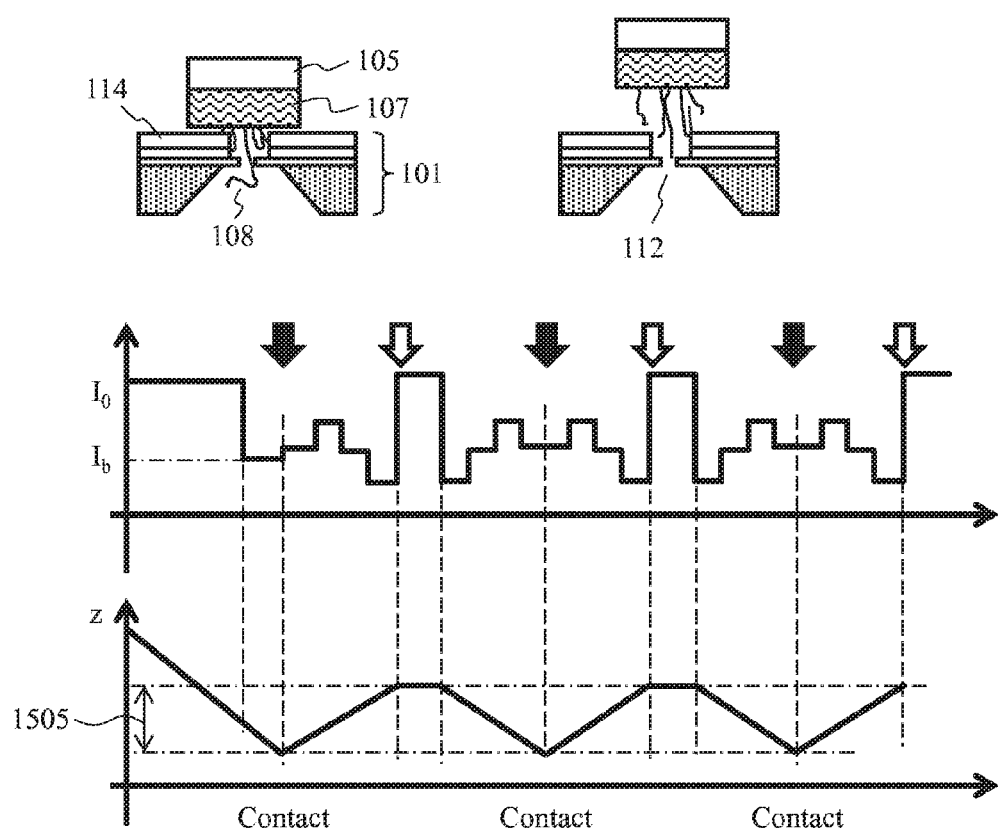
FIG. 19 is an explanatory view illustrating an exemplary method for reading the base sequence of DNA.

FIG. 19 is an explanatory view showing an exemplary method for reading the base sequence of DNA as a biomolecule. The upper view of FIG. 19 shows the two representative positional relationships between the biomolecule-immobilized probe and the nanopore device during analysis of the base sequence of DNA. A change in ion current is shown in the middle view of FIG. 19, and a displacement of the biomolecule-immobilized probe 107 is shown in the lower view. The displacement z shown in the lower view corresponds to the distance between the biomolecule-immobilized probe 107 and the nanopore device 101. In addition, FIG. 19 also shows the time point when the drive direction of the biomolecule-immobilized probe 107 by the drive mechanism 105 is changed and the positional relationship between the biomolecule-immobilized probe 107 and the nanopore device 101 at that point. The solid arrows in the middle view each indicate a first positional relationship shown on the left side of the upper view, and the hollow arrows each indicate a second positional relationship shown on the right side of the upper view.

When the biomolecule-immobilized probe 107 is driven downward along the z-axis by the drive mechanism 105, a free end of the biomolecule 108 enters the nanopore, and the biomolecule is then elongated between the end immobilized on the biomolecule-immobilized probe and the nanopore. At this time, the amount of ion current decreases in accordance with the average diameter of the biomolecule 108, and thus becomes $I_b$. When a biomolecule enters the potential gradient 201 from the outside, the biomolecule is folded. Therefore, the biomolecule passes through the nanopore not at the movement speed of the biomolecule-immobilized probe but at the speed of the free electrophoresis of the biomolecule. The ion current value at that time shows not a current value derived from each base, but the average current value $I_b$ dependent on the average diameter of the biomolecule.

After that, the biomolecule-immobilized probe 107 is driven further downward along the z-axis by the drive mechanism 105, but the downward movement of the biomolecule-immobilized probe 107 along the z-axis is hindered by the space forming film 114, and the movement thus stops. The positional relationship among the biomolecule-immobilized probe 107, the biomolecule 108, and the nanopore device 101 at that time is shown as a first positional relationship in the upper left view of FIG. 19.

The translocation speed of the biomolecule that is pulled upward afterwards becomes equal to the driving speed of the biomolecule-immobilized probe 107. Therefore, the biomolecule can be translocated at a speed that is necessary to decompose a single base (<3.4 nm/ms). Thus, a signal that reflects the base sequence of the biomolecule can be obtained. In this manner, in the process in which the biomolecule-immobilized probe 107 is driven upward along the z-axis by the drive mechanism 105, the sequence information on the biomolecule 108 moving in the nanopore 112 can be read. While a free end, which is not immobilized, of the biomolecule 108 is located in the potential gradient 201 around the nanopore after having come out of the nanopore 112, the biomolecule 108 receives forces in opposite directions from both the biomolecule-immobilized probe 107 and the potential gradient 201 around the nanopore, and thus is elongated. The upper right view in FIG. 19 shows the relationship among the biomolecule-immobilized probe 107, the biomolecule 108, and the nanopore device 101 at that time. As the biomolecule 108 comes out of the nanopore 112, the amount of ion current returns to $I_0$. The change in the current value is detected, and the drive of the biomolecule-immobilized probe 107 by the drive mechanism 105 is then stopped.

Again, the biomolecule-immobilized probe 107 is driven downward along the z-axis by the drive mechanism 105 so that the biomolecule 108 is passed through the nanopore from the side of a free end thereof, and the base sequence of the biomolecule 108 is read in this period. At this time, the biomolecule 108 is elongated as a whole because the free end of the biomolecule 108 is located in the potential gradient 201 in a state in which the other end of the biomolecule 108 is immobilized on the biomolecule-immobilized probe 107. Thus, as the biomolecule passes through the nanopore from the side of a free end thereof at the driving speed of the drive mechanism 105, a signal can be read with high accuracy. In addition, as the sequence read while the biomolecule-immobilized probe 107 was driven upward along the z-axis is read from a reverse direction, an ion current that changes symmetrically by reflecting the read sequence is measured. When the biomolecule-immobilized probe 107 contacts the space forming film 114 again, the drive of the biomolecule-immobilized probe 107 stops.

After that, the biomolecule-immobilized probe 107 is repeatedly moved up and down so that reading is continued until the necessary accuracy of sequence reading is obtained. The displacement 1505 of the biomolecule-immobilized probe 107 from the contact position with the nanopore device 101 to the position where the ion current value becomes $I_0$ reflects the length of the biomolecule.

Embodiment 3

Next, an embodiment in which nanopore devices are arranged in parallel in the biomolecule measurement system will be described. The biomolecule measurement system of the present invention is highly compatible with nanopore devices that are arranged in parallel. When nanopore devices are arranged in parallel, it becomes possible to concurrently measure the same type of biomolecules. Therefore, the throughput can be improved. Herein, three types of parallel arrangement are exemplarily shown.

Figure 20:
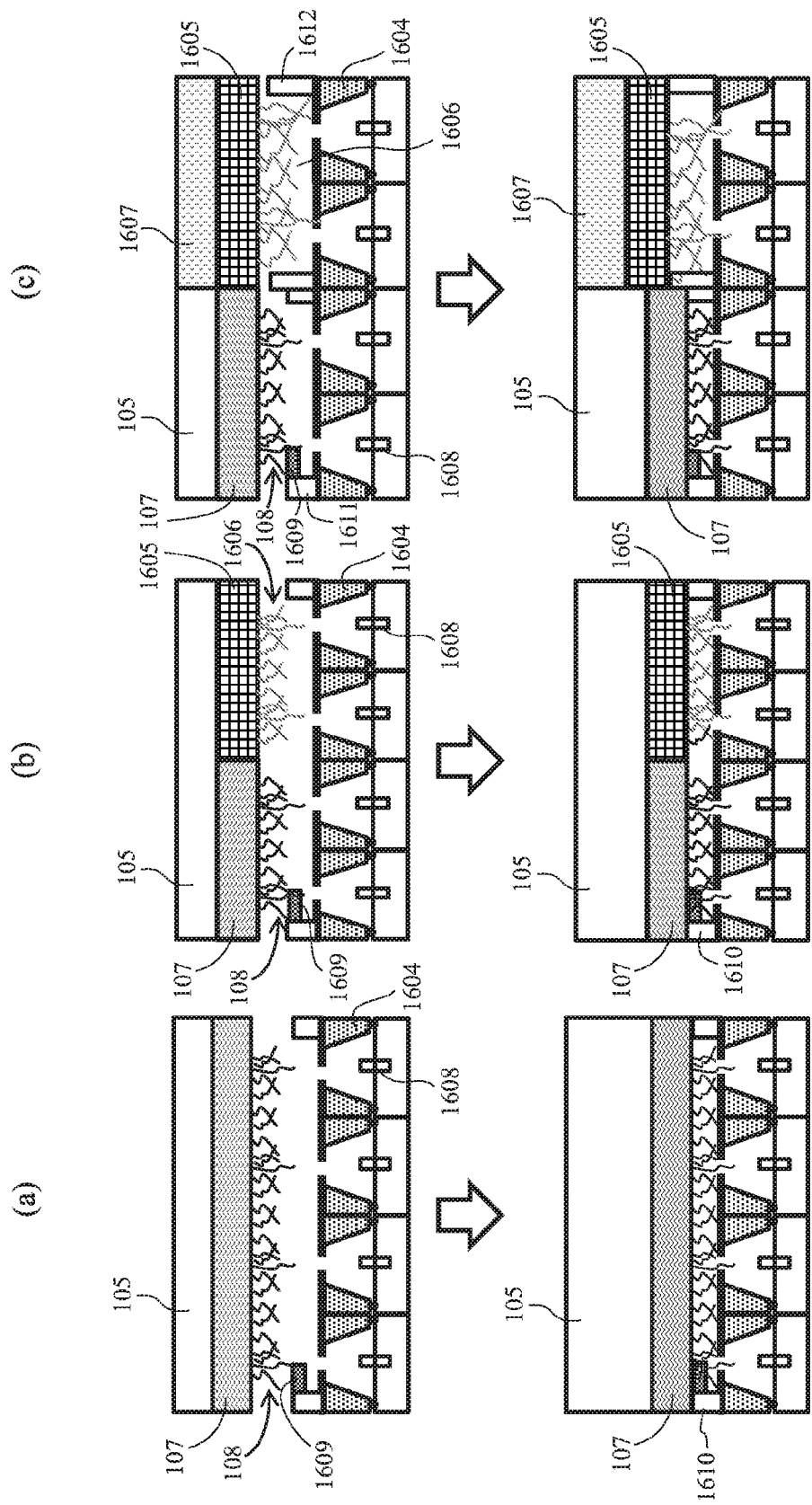
FIGS. 20(a) to 20(c) are cross-sectional schematic views showing exemplary biomolecule measurement systems each having nanopore devices that are arranged in parallel.

FIG. 20(*a*) is a cross-sectional schematic view showing a first example of a biomolecule measurement system having nanopore devices that are arranged in parallel. In this example, a plurality of nanopore devices 1604 are arranged adjacent to one another in the horizontal direction, and a common drive mechanism 105 and a common biomolecule-immobilized probe 107 are arranged above the plurality of nanopore devices 1604. The biomolecule-immobilized probe 107 has an area that can sufficiently cover the entirety of the plurality of nanopore devices. Each of the plurality of nanopore devices 1604 arranged in parallel has an independent liquid tank, and one of array electrodes 1608 is arranged in the liquid tank of each nanopore device. Each array electrode 1608 is connected to an amplifier. A common liquid tank is provided above the plurality of nanopore devices 1604 arranged in parallel, and a counter electrode (common electrode) 1609 that is common to the array electrodes 1608 is arranged in the liquid tank. Common space forming films 1610 that are common to the plurality of nanopore devices arranged in parallel are provided on the lateral sides of the nanopore devices. The liquid tank of each nanopore device 1604 communicates with the upper liquid tank via each nanopore provided in the nanopore device 1604.

The lower surface of the biomolecule-immobilized probe 107 has a plurality of biomolecules 108 bound thereto. When the drive mechanism 105 is moved downward along the z-axis, the biomolecules 108 on the biomolecule-immobilized probe 107 pass through the nanopores provided in the respective nanopore devices. In this embodiment, a plurality of biomolecules can be concurrently measured using a plurality of nanopores. Therefore, the measurement throughput is increased.

FIG. 20(*b*) is a cross-sectional schematic view showing a second example of a biomolecule measurement system having nanopore devices that are arranged in parallel. In this example, a drive mechanism 105 is arranged above a plurality of nanopore devices 1604 arranged in parallel. An array electrode 1608 is connected to each nanopore device 1604. A common liquid tank is provided above the plurality of nanopore devices 1604, and a counter electrode 1609 that is common to each array electrode is disposed. Common space forming films 1610 that are common to the plurality of nanopore devices 1604 arranged in parallel are provided on the lateral sides of the nanopore devices. A plurality of biomolecule-immobilized probes are connected to the drive mechanism 105, and different types of biomolecules are immobilized on the respective biomolecule-immobilized probes. Accordingly, property analysis of different biomolecules can be performed concurrently.

In the example shown in the drawing, two biomolecule-immobilized probes that are a first biomolecule-immobilized probe 107 and a second biomolecule-immobilized probe 1605 are connected to the drive mechanism 105; the first biomolecule-immobilized probe has first biomolecules 108 bound thereto; and the second biomolecule-immobilized probe 1605 has second biomolecules 1606 bound thereto. According to this embodiment, not only can a plurality of nanopores be used for one type of samples, but also a plurality of types of samples can be measured concurrently, whereby the measurement throughput is increased.

FIG. 20(*c*) is a cross-sectional schematic view showing a third example of a biomolecule measurement system having nanopore devices that are arranged in parallel. In this example, a plurality of drive mechanisms are arranged above a plurality of nanopore devices 1604 arranged in parallel. Biomolecule-immobilized probes are connected to the respective drive mechanisms, and different types of biomolecules are immobilized on the respective biomolecule-immobilized probes. A space forming film can also be provided for each biomolecule-immobilized probe.

In the example shown in the drawing, a first drive mechanism 105 and a second drive mechanism 1607 are arranged; the first biomolecule-immobilized probe 107 has first biomolecules 108 bound thereto; and the second biomolecule-immobilized probe 1605 has second biomolecules 1606 bound thereto. A first space forming film 1611 is provided for the first biomolecule-immobilized probe 107, and a second space forming film 1612 is provided for the second biomolecule-immobilized probe 1605. The first space forming film 1611 and the second space forming film 1612 have different thicknesses. Accordingly, even biomolecules with different lengths can be independently adjusted in height. The space forming film formed on the nanopore device has a slit formed thereon so that a solution that fills a region above the nanopores does not become independent for each sample when the biomolecule-immobilized probe moves downward and contacts the space forming film. Accordingly, an electrode that is disposed above the nanopores may be only the common electrode 1609.

In any of the examples, the relationship between the number a of nanopores and the number b of biomolecules on the biomolecule-immobilized probe satisfies a<b. Thus, densely immobilizing biomolecules on the biomolecule-immobilized probe will surely allow any of the biomolecules to be introduced into the nanopores when the biomolecule-immobilized probe is lowered perpendicularly toward the nanopore devices.

Embodiment 4

An embodiment in which magnetic beads are used as another means for immobilizing biomolecules on the biomolecule-immobilized probe will be described. Herein, an example in which the system shown in FIG. 20(a) is used as a biomolecule measurement system will be described. It should be noted that the biomolecule-immobilized probe is formed using a magnetic material.

Figure 21:
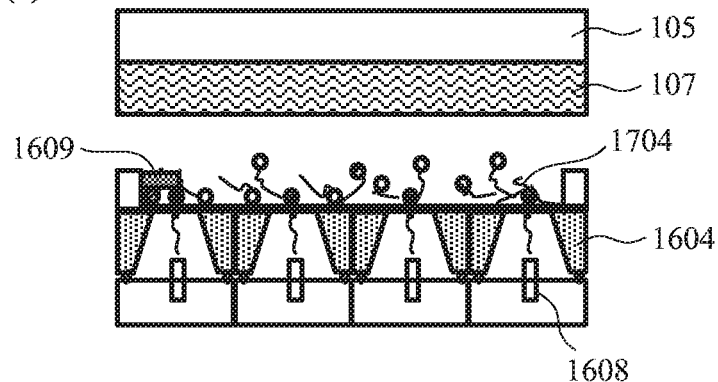
FIGS. 21(a) to 21(c) are cross-sectional schematic views illustrating the measurement procedures using magnetic beads.
Figure 21:
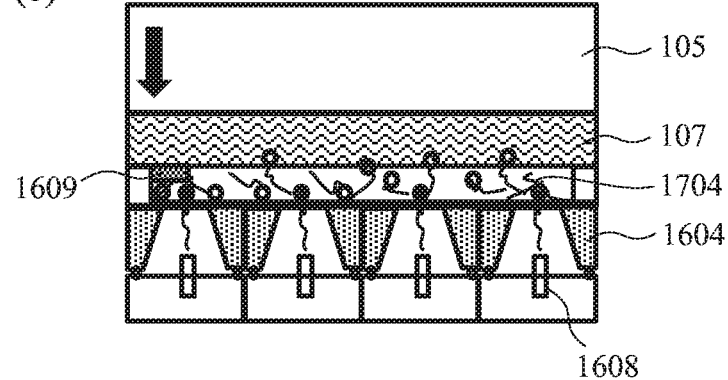
Figure 21:
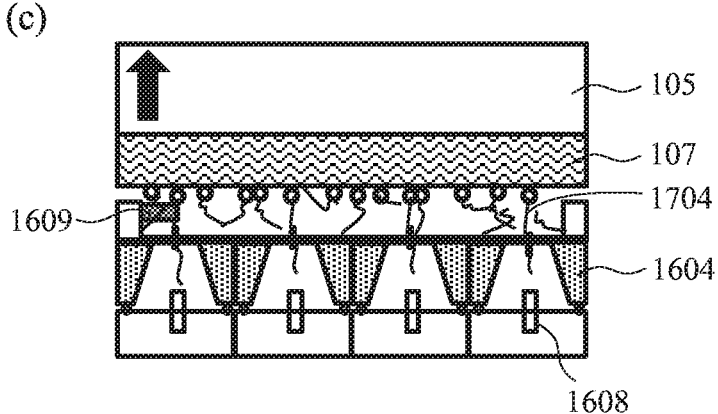

FIGS. 21(a) to 21(c) are cross-sectional schematic views illustrating the procedures for immobilizing biomolecules on the biomolecule-immobilized probe using magnetic beads and performing measurement. As the biomolecules, biomolecules that have been immobilized on magnetic beads in advance are prepared.

In the first step, as shown in FIG. 21(a), a voltage is applied across the Ag/AgCl electrodes 1608 arranged in the respective nanopore devices 1604 arranged in parallel and the common electrode 1609 so that an electric field is generated in an electrolytic solution around the nanopores and the biomolecules 1704 immobilized on the magnetic beads are thus allowed to migrate through electrophoresis and are introduced into the nanopores of the nanopore devices 1604 arranged in parallel. Herein, an ion current derived from each nanopore is monitored so that an effective nanopore device having a nanopore into which a biomolecule has been introduced can be confirmed from the rate of change in ion current.

In the second step, as shown in FIG. 21(b), the application of a voltage via the nanopores in the first step is continued, and the biomolecule-immobilized probe 107 is driven toward the nanopore devices 1604 by the drive mechanism 105 as shown by the arrow so that the magnetic beads are pulled toward the biomolecule-immobilized probe 107 by a magnetic force and thus are immobilized thereon.

In the third step, as shown in FIG. 21(c), the biomolecule-immobilized probe 107 is driven by the drive mechanism 105 at a controlled speed in the direction away from the nanopore devices 1604 as shown by the arrow, and an ion current that changes due to the biomolecule moving in the nanopore is detected with an ammeter, and thus is recorded in a PC. The drive mechanism 105 having a piezoelectric element can drive the biomolecule-immobilized probe 107 at a given speed. When the sequence of DNA is read, in particular, high-accuracy reading becomes possible by moving DNA, which has been immobilized on a magnetic bead, in a nanopore at a speed of less than or equal to 3.4 nm/ms.

According to this embodiment, the initial alignment between nanopores and biomolecules is not necessary. Further, as biomolecules can be introduced into nanopores by being diffused within an electric field generated around the nanopores, it is possible to reduce the probability that the nanopores arranged in parallel include nanopores through which biomolecules cannot pass.

Embodiment 5

Figure 22:
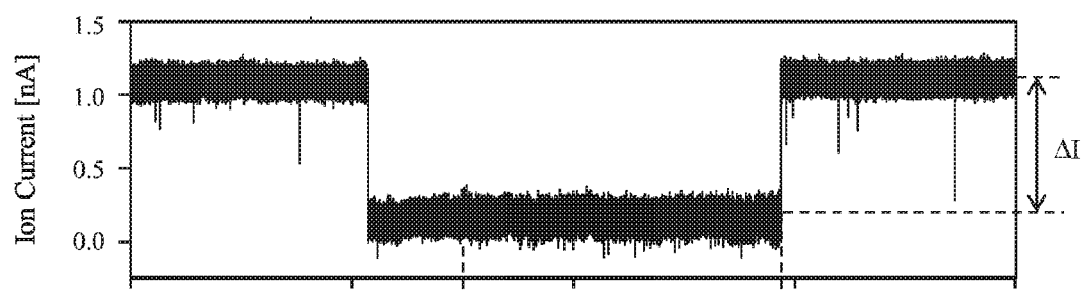
FIGS. 22(a) and 22(b) are views in which a blocking current disappears along with the drive of a biomolecule-immobilized probe.
Figure 22:
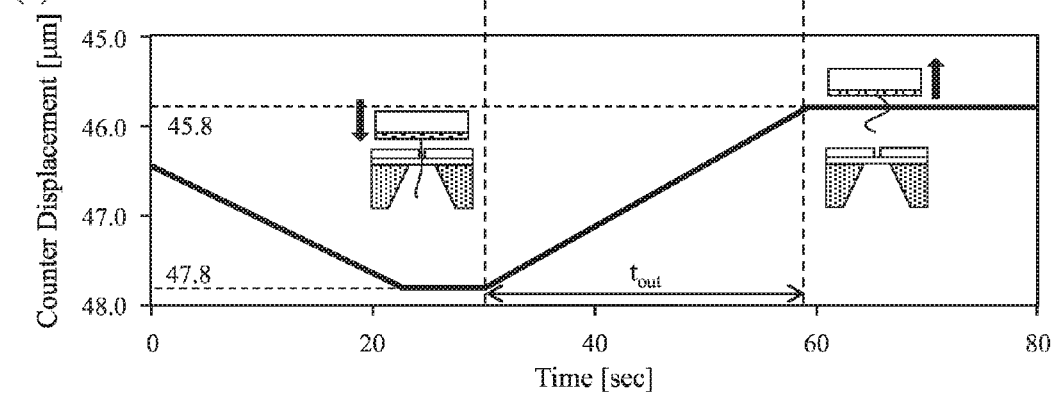

FIGS. 22(a) and 22(b) are views in which a blocking current disappears along with the drive of the biomolecule-immobilized probe by the drive mechanism.

The biomolecule measurement system shown in FIG. 1 was used, and an biomolecule-immobilized probe with a surface modified with APTES/glutaraldehyde, which has ss-poly(dA) with a chain length of 5 k immobilized thereon, was moved close to a nanopore of a nanopore device. Consequently, as shown in FIG. 22(a), a blocking signal was confirmed, but the blocking signal disappeared when the biomolecule-immobilized probe was moved away from the nanopore device. FIG. 22(b) shows a trajectory of the biomolecule-immobilized probe in the same time period as that in FIG. 22(a). As a counter displacement increases, the nanopore device and the biomolecule-immobilized probe are located closer to each other. The drive of the biomolecule-immobilized probe by the drive mechanism was stopped after about 1 second has elapsed after confirming a decrease in ion current. After about 10 seconds, the distance between the nanopore device and the biomolecule-immobilized probe starts to be increased, and at a time point when an ion current has increased again, (after 30 seconds have elapsed), the drive by the drive mechanism was stopped. This shows that DNA has been introduced into and pulled from a nanopore by the drive of the biomolecule-immobilized probe by the drive mechanism because when the biomolecule-immobilized probe with DNA immobilized thereon was moved close to the nanopore, an ion current decreased, but when the biomolecule-immobilized probe was moved away from the nanopore, the current value returned to the original value.

Figure 23:
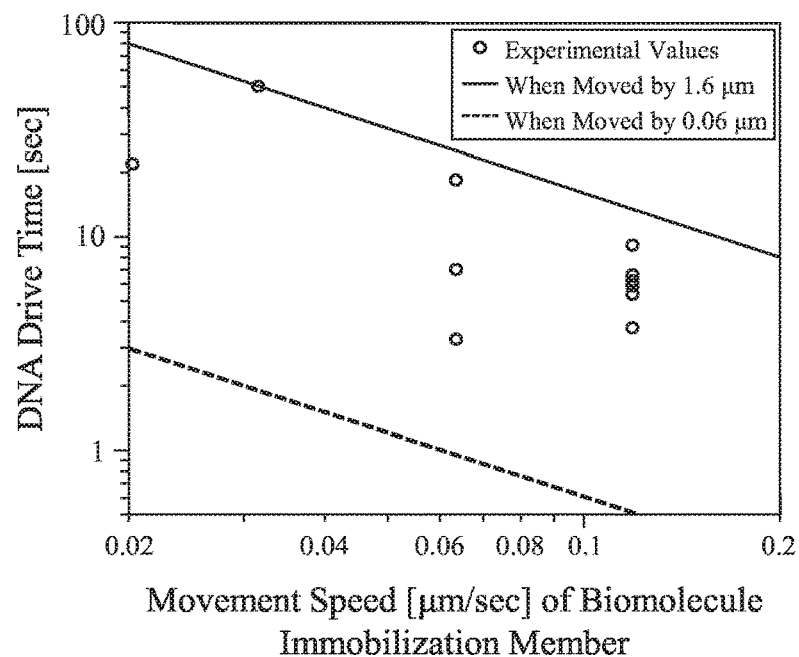
FIG. 23 is a view showing the relationship between the movement speed of a biomolecule-immobilized probe and the DNA drive time.

The duration (DNA drive time) from the time when the drive mechanism started to be driven in order to move the biomolecule-immobilized probe away from the nanopore device to the time when the blocking signal disappeared is defined by $t_{out}$ as shown in FIG. 22(b). Meanwhile, the movement speed of the biomolecule-immobilized probe was determined from the relationship with the counter speed in accordance with the preset speed of the drive mechanism. FIG. 23 shows the relationship of the DNA drive time ($t_{out}$) acquired relative to the movement speed of each biomolecule-immobilized probe. The plots in the graph show the experimental values. Herein, the DNA driven distance, that is, the maximum length of DNA introduced into a nanopore in each measurement is determined by the position where the drive of the biomolecule-immobilized probe has stopped after the nanopore had been blocked by the DNA. The drive of the biomolecule-immobilized probe by the drive mechanism is manually stopped after visually checking a blocking signal that indicates that DNA has entered a nanopore. Thus, it is considered that it takes about one second at the shortest after DNA has actually entered a nanopore until the drive of the biomolecule-immobilized probe stops. Therefore, DNA with a length of about 60 to 100 nm at the shortest will surely enter a nanopore.

In FIG. 23, the solid line indicates the calculated value of the maximum DNA drive time determined from the length of the immobilized DNA. In addition, the dashed line indicates the calculated value of the minimum DNA drive time that is required for DNA of 60-nm length to enter a nanopore. As the experimentally measured DNA drive times are located in the range of from the solid line to the dashed line, it is considered that the acquired blocking signals derive from DNA on the biomolecule-immobilized probe and thus that the actually measured values are appropriate. In addition, as the movement speed of the biomolecule-immobilized probe is slower, the actually measured DNA drive times are distributed in the direction in which the DNA drive time becomes longer. This is considered to be due to the reason that DNA on the biomolecule-immobilized probe is translocated in a nanopore while depending on the driving speed of the drive mechanism.

Figure 24:
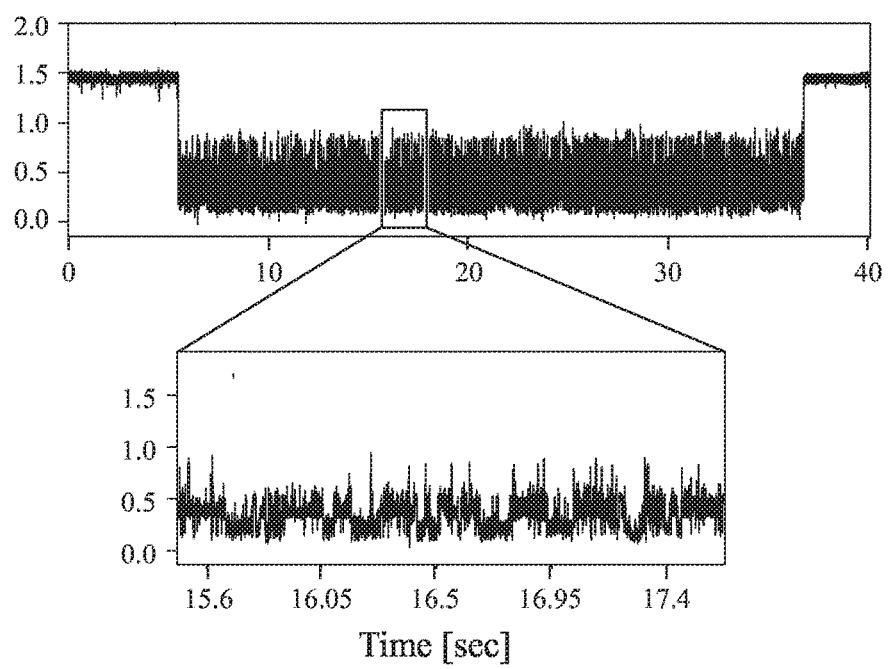
FIG. 24 is a view showing an example in which an ion current of mixed molecules of two types of polymers ((dA50dC50)m) is traced.

FIG. 24 is a view showing the results of similarly binding molecules ((dA50dC50)m), which contain repeatedly extended polymers of dA50dC50, to the biomolecule-immobilized probe and performing measurement. When the biomolecule-immobilized probe was moved close to the nanopore device, a blocking signal such as the one acquired in FIG. 22(a) was confirmed. When the current after the blocking was analyzed, a two-level signal was obtained. As described above, when biomolecules were bound to the biomolecule-immobilized probe and the molecule passing speed was lowered, it became possible to measure a view in which the strengths of blocking signals differ depending on the types of the molecules.

The present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add/remove/substitute a configuration of another embodiment.

REFERENCE SIGNS LIST

100 Biomolecule property analyzing system
101 Nanopore device
102 Electrolytic solution
103a, 103b Ag/AgCl electrodes
104 Power supply
105 Drive mechanism
106 Drive mechanism control unit
107 Biomolecule-immobilized probe
108 Biomolecule
109 Ammeter
110 PC
111 Connecting unit
112 Nanopore
113 Thin film
114 Space forming film 201 Potential gradient
403 Electrolytic solution containing biomolecules
601 Space forming film
702a, 702b Electrodes
801 to 804 Electrodes
901 Linker
1206 Switching unit
1704 Biomolecule immobilized on a bead

The invention claimed is:

1. A biomolecule measurement system comprising:
a first liquid tank adapted to be filled with an electrolytic solution;
a second liquid tank adapted to be filled with the electrolytic solution;
a thin film with a nanopore being provided between the first liquid tank and the second liquid tank so as to allow the first liquid tank and the second liquid tank to communicate with each other via the nanopore, the thin film having a first exposed surface with the nanopore facing the first liquid tank to be exposed to the electrolytic solution in the first liquid tank;
a biomolecule-immobilized member disposed in the first liquid tank and having a biomolecule-immobilized region facing the first exposed surface of the thin film with the nanopore, the biomolecule-immobilized region having a surface area with a larger size than a surface area of the first exposed surface of the thin film facing the first liquid tank, the biomolecule-immobilized member being driven in a direction toward and away from the first exposed surface of the thin film;
a first electrode provided in the first liquid tank;
a second electrode provided in the second liquid tank;
a stopper disposed between the biomolecule-immobilized member and the first exposed surface of the thin film to prevent contact between the biomolecule-immobilized member and the thin film, the stopper covering an unexposed surface of the thin film surrounding the first exposed surface of the thin film to provide a space between the first exposed surface of the thin film and the biomolecule-immobilized region of the biomolecule-immobilized member, the stopper having an opening to allow the first exposed surface of the thin film to be exposed to the biomolecule-immobilized region of the biomolecule-immobilized member;
a power supply configured to apply a voltage across the first electrode and the second electrode; and
an ammeter to measure an ion current flowing between the first electrode and the second electrode,
wherein the ammeter is configured to acquire sequence information on a biomolecule having one end immobilized on the biomolecule-immobilized probe on the basis of an ion current that is measured when the biomolecule passes through the nanopore.

2. The biomolecule measurement system according to claim 1, wherein a plurality of biomolecules are immobilized on the biomolecule-immobilized member.

3. The biomolecule measurement system according to claim 1, wherein the biomolecule-immobilized member does not deform by an amount of greater than or equal to 0.3 nm upon receiving a force of 240 nN.

4. The biomolecule measurement system according to claim 1, wherein a Young's modulus of the biomolecule-immobilized member is, provided that a cross-sectional area of the biomolecule-immobilized member is S and a length of the biomolecule-immobilized member is L, greater than or equal to $0.007 \, (L/S)[N/mm^2]$.

5. The biomolecule measurement system according to claim 1, wherein a material of the biomolecule-immobilized member is one of Si, SiO, SiN, Au, Ag, Pt, Ti, TiN, or a magnetic material.

6. The biomolecule measurement system according to claim 1, wherein the biomolecule is immobilized on the biomolecule-immobilized member directly through covalent binding of organic molecules, ion binding, or electrostatic interaction.

7. The biomolecule measurement system according to claim 6, wherein the biomolecule is bound through covalent binding using a Si/APTES/glutaraldehyde/amino-modified biomolecule, through gold-thiol binding, through ion binding using biotin-SA, or through electrostatic interaction using an APTES/amino-modified biomolecule.

8. The biomolecule measurement system according to according to claim 1, wherein the biomolecule is a nucleic acid or a protein.

9. The biomolecule measurement system according to claim 1, wherein the biomolecule is immobilized on the biomolecule-immobilized member together with a short-chain polymer with a modified end.

10. The biomolecule measurement system according to claim 1,
    wherein the stopper is provided on at least a part of a region outside the thin film or a region outside a portion, which is opposite the thin film, of the biomolecule-immobilized region of the biomolecule-immobilized member, and
    wherein the stopper is a space forming film adapted to form a space between the biomolecule-immobilized member and the thin film.

11. The biomolecule measurement system according to claim 1, wherein the stopper comprises a pair of electrodes provided on at least a part of a region outside a portion, which corresponds to the thin film, of an upper surface of the nanopore device or a lower surface of the biomolecule-immobilized member.

12. The biomolecule measurement system according to claim 1, wherein the biomolecule-immobilized member is driven at a speed of 34 nm/sec to 34 µm/sec.

13. The biomolecule measurement system according to claim 1, further comprising a piezoelectric element to drive the biomolecule-immobilized member.

14. The biomolecule measurement system according to claim 1, comprising:
    a plurality of the thin films each having a nanopore and being arranged adjacent to each other along a lateral direction, and
    a plurality of the second liquid tanks, second electrodes, and ammeters that are provided for the respective laterally arranged thin films,
    wherein the first liquid tank, the biomolecule-immobilized member, the first electrode, and the stopper are provided in common to the plurality of laterally arranged thin films.

15. The biomolecule measurement system according to claim 1, comprising:
    a plurality of the thin films each having a nanopore and being arranged adjacent to each other along a lateral direction,
    a plurality of the second liquid tanks, second electrodes, and ammeters that are provided for the respective laterally arranged thin films, and
    a plurality of the biomolecule-immobilized members,
    wherein the first liquid tank, the first electrode, and the stopper are provided in common to the plurality of laterally arranged thin films.

16. The biomolecule measurement system according to claim 1, comprising:
    a plurality of the thin films each having a nanopore and being arranged adjacent to each other along a lateral direction,
    a plurality of the second liquid tanks, second electrodes, and ammeters that are provided for the respective laterally arranged thin films, and
    a plurality of sets each including the biomolecule-immobilized member and the stopper that are provided for the respective laterally arranged thin films,
    wherein the first liquid tank and the first electrode are provided in common to the plurality of laterally arranged thin films.

* * * * *